US009492141B2

(12) United States Patent
Toma et al.

(10) Patent No.: US 9,492,141 B2
(45) Date of Patent: Nov. 15, 2016

(54) ULTRASONIC IMAGE GENERATING DEVICE AND IMAGE GENERATING METHOD

(75) Inventors: Tadamasa Toma, Osaka (JP); Jun Ohmiya, Kyoto (JP); Bunpei Toji, Gifu (JP)

(73) Assignee: KONICA MINOLTA, INC., Tokyo (JP)

( * ) Notice: Subject to any disclaimer, the term of this patent is extended or adjusted under 35 U.S.C. 154(b) by 918 days.

(21) Appl. No.: 13/591,304

(22) Filed: Aug. 22, 2012

(65) Prior Publication Data
US 2012/0316441 A1 Dec. 13, 2012

Related U.S. Application Data

(63) Continuation of application No. PCT/JP2011/006960, filed on Dec. 13, 2011.

(30) Foreign Application Priority Data

Dec. 24, 2010 (JP) ................................. 2010-287291

(51) Int. Cl.
*A61B 8/00* (2006.01)
*A61B 6/00* (2006.01)
*A61B 8/06* (2006.01)
*A61B 8/08* (2006.01)

(52) U.S. Cl.
CPC ........... *A61B 8/4245* (2013.01); *A61B 8/4263* (2013.01); *A61B 8/483* (2013.01); *A61B 8/523* (2013.01); *A61B 6/4417* (2013.01); *A61B 8/06* (2013.01); *A61B 8/0891* (2013.01); *A61B 8/485* (2013.01); *A61B 8/488* (2013.01)

(58) Field of Classification Search
CPC .... A61B 6/4417; A61B 8/06; A61B 8/0891; A61B 8/4245; A61B 8/4263
See application file for complete search history.

(56) References Cited

U.S. PATENT DOCUMENTS

| 4,984,157 | A | * | 1/1991 | Cline et al. ................... 345/424 |
| 5,754,618 | A | * | 5/1998 | Okamoto et al. ................ 378/4 |
| 6,988,991 | B2 | | 1/2006 | Kim et al. |
| 2004/0006273 | A1 | | 1/2004 | Kim et al. |
| 2006/0100512 | A1 | * | 5/2006 | Lee ............................... 600/437 |
| 2007/0287915 | A1 | * | 12/2007 | Akaki et al. ................... 600/443 |

FOREIGN PATENT DOCUMENTS

| JP | 2003-325519 | 11/2003 |
| JP | 3619425 | 2/2005 |
| JP | 2006-116316 | 5/2006 |
| JP | 2008-125692 | 6/2008 |

OTHER PUBLICATIONS

International Search Report issued Jan. 17, 2012 in International (PCT) Application No. PCT/JP2011/006960.

* cited by examiner

*Primary Examiner* — Unsu Jung
*Assistant Examiner* — Saurel J Selkin
(74) *Attorney, Agent, or Firm* — Holtz, Holtz & Volek PC

(57) ABSTRACT

An ultrasonic image generating device which generates a cross-sectional image of a specific cross-section of a subject from ultrasonic images obtained by scanning the subject from a plurality of directions using an ultrasonic probe, includes: a cross-section position identifying unit which obtains cross-section information indicating a position and an orientation of the specific cross-section; a positional information obtaining unit which obtains positional information including a position and an orientation of each of the ultrasonic images of the subject; a reference image selecting unit which selects at least one of the ultrasonic images as a reference image, the at least one of the ultrasonic images having a distance from the specific cross-section that is less than a first threshold and an orientation difference from the specific cross-section that is less than a second threshold; and a cross-sectional image generating unit which generates the cross-sectional image using the reference image.

13 Claims, 22 Drawing Sheets

ULTRASONIC IMAGE GENERATING DEVICE AND IMAGE GENERATING METHOD

CROSS REFERENCE TO RELATED APPLICATIONS

This is a continuation application of PCT Patent Application No. PCT/JP2011/006960 filed on Dec. 13, 2011, designating the United States of America, which is based on and claims priority of Japanese Patent Application No. 2010-287291 filed on Dec. 24, 2010. The entire disclosures of the above-identified applications, including the specifications, drawings and claims are incorporated herein by reference in their entirety.

FIELD

One or more exemplary embodiments disclosed herein relate generally to ultrasonic image generating devices and image generating methods, and in particular, to an ultrasonic image generating device which generates cross-sectional images of specific cross-sections of a subject from ultrasonic images obtained by scanning the subject from a plurality of directions using an ultrasonic probe.

BACKGROUND

An X-ray diagnostic device, a magnetic resonance (MR) diagnostic device, and an ultrasonic diagnostic device are widely used as diagnostic imaging devices for examining bodies. In particular, the ultrasonic diagnostic device has advantages such as its non-invasive nature and real-time performance and is widely used for diagnostics including medical examinations. The ultrasonic diagnostic device is used in diagnostics for a variety of regions of the body including heart, liver, and a breast. One of the most important regions is the breast due to high morbidity and increased number of patients of breast cancers.

Hereinafter, a description is given of an example where a breast is examined. For ultrasonically examining a breast, imaging is performed while scanning an ultrasonic probe over the breast. Here, due to contact state between the ultrasonic probe and the breast or deformity of the breast, image degradation of the ultrasonic images or deformation of mammary tissue occurs. Therefore, ultrasonic images taken from one direction may not be sufficient for an accurate diagnosis.

In view of this, a method has been recently gaining attention where a three-dimensional tissue structure within the breast is constructed from temporally-different ultrasonic images obtained by scanning using a ultrasonic probe. The method increases diagnostic accuracy by observing the same region from different directions. For constructing the three-dimensional tissue structure, each ultrasonic image is mapped into the three-dimensional space based on the positional information of the ultrasonic image (position and orientation of the ultrasonic probe). The positional information is obtained from, for example, a camera, various types of sensors such as a magnetic sensor and an acceleration sensor, or a robotic arm.

CITATION LIST

Patent Literature

[PTL 1]
Japanese Patent No. 3619425

SUMMARY

Technical Problem

However, there is a need for an ultrasonic image generating device with higher accuracy.

One non-limiting and exemplary embodiment provides an ultrasonic image generating device with an increased accuracy.

Solution to Problem

In one general aspect, the techniques disclosed here feature an ultrasonic image generating device which generates a cross-sectional image of a specific cross-section of a subject from a plurality of ultrasonic images obtained by scanning the subject from a plurality of directions using an ultrasonic probe, and includes: a cross-section position identifying unit which obtains cross-section information indicating a position and an orientation of the specific cross-section; a positional information obtaining unit which obtains positional information including a position and an orientation of each of the ultrasonic images of the subject; a reference image selecting unit which selects at least one of the ultrasonic images as a reference image, the at least one of the ultrasonic images having a distance from the specific cross-section that is less than a first threshold and an orientation difference from the specific cross-section that is less than a second threshold; and a cross-sectional image generating unit which generates the cross-sectional image using the reference image.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

One or more exemplary embodiments or features disclosed herein provide an ultrasonic image generating device with an increased accuracy.

BRIEF DESCRIPTION OF DRAWINGS

These and other advantages and features will become apparent from the following description thereof taken in conjunction with the accompanying Drawings, by way of non-limiting examples of embodiments disclosed herein.

DESCRIPTION OF EMBODIMENT(S)

(Underlying Knowledge Forming Basis of the Present Disclosure)

Figure 16:
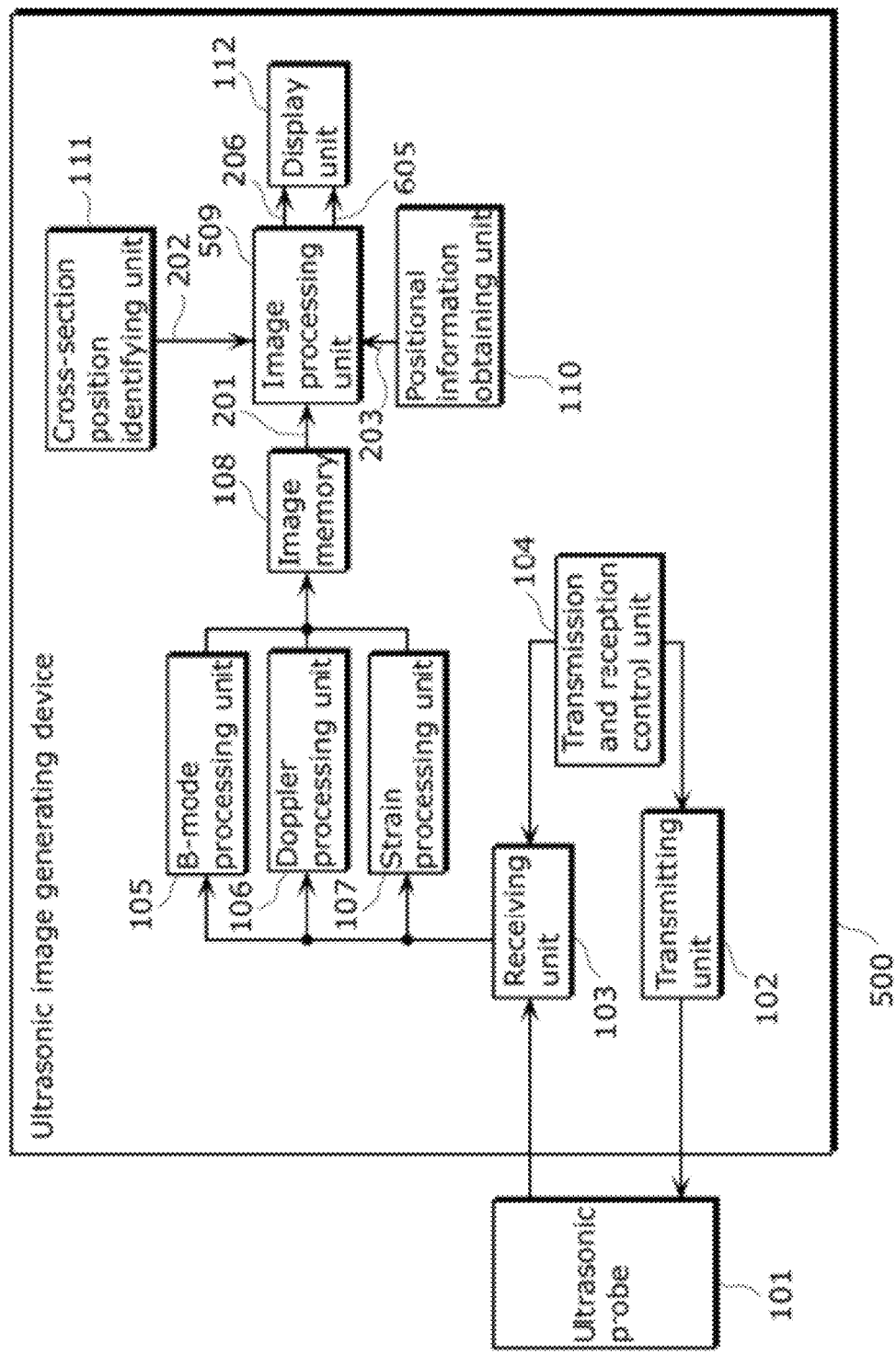
FIG. 16 is a block diagram illustrating a configuration of an ultrasonic image generating device according to a reference example.
Figure 17:
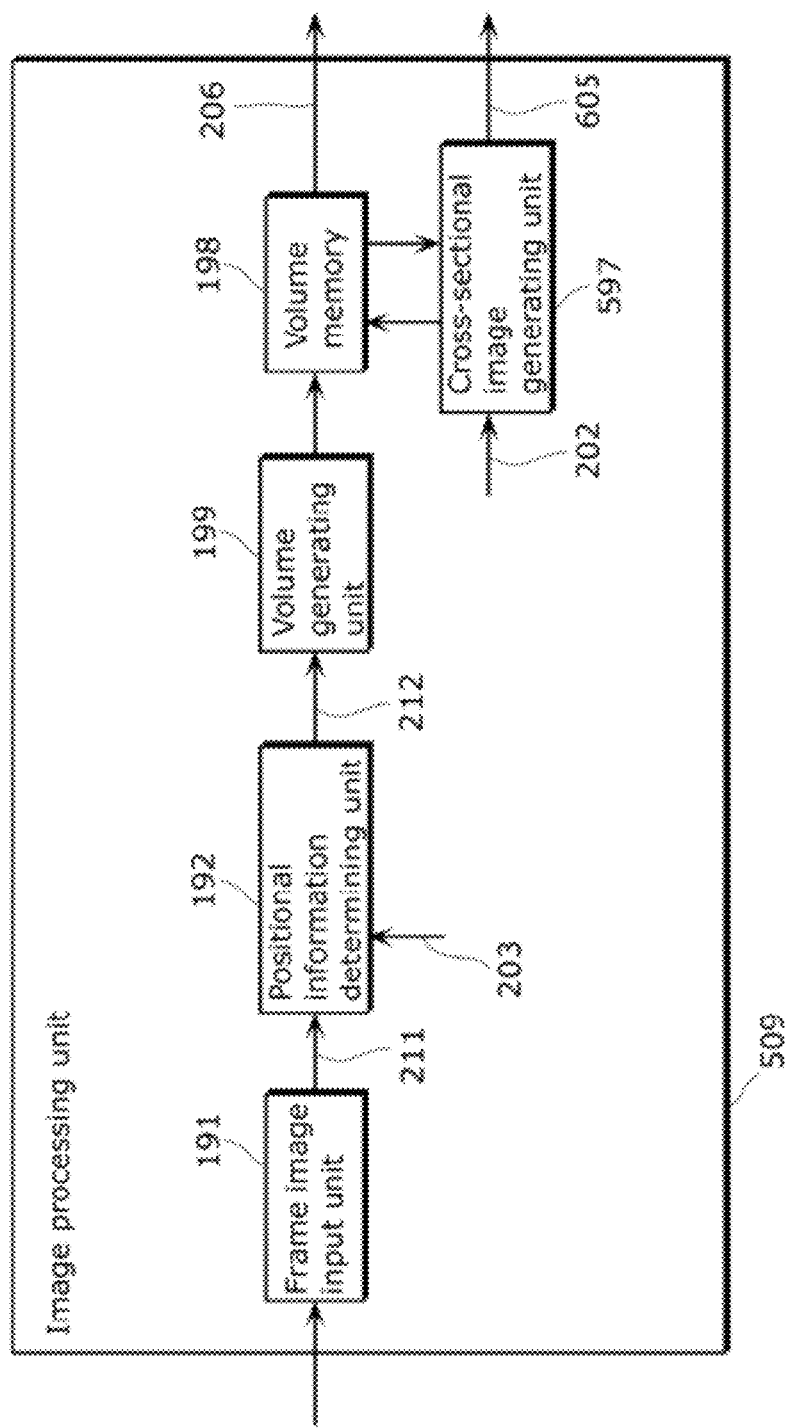
FIG. 17 is a block diagram illustrating a configuration of an image processing unit according to a reference example.

Referring to FIG. 16 and FIG. 17, the following describes an ultrasonic diagnostic device, according to a reference example, which reconstructs a three-dimensional tissue structure based on the positional information at the time of ultrasonic image obtainment and which synthesizes arbitrary cross-sectional images from the three-dimensional tissue structure.

FIG. 16 is a block diagram illustrating an overall configuration of an ultrasonic image generating device 500 according to a reference example (an ultrasonic diagnostic device). Elements such as piezoelectric elements arranged in an ultrasonic probe 101 generate ultrasonic signals based on driving signals provided from a transmitting unit 102. The ultrasonic signals are reflected from the structure in a body such as mammary gland and muscle. Part of the reflected components return to the ultrasonic probe 101 and is received by the ultrasonic probe 101. A receiving unit 103 generates reception radio frequency (RF) signals by performing, on the reflected signals received, amplification and analog-to-digital (A/D) conversion, and by, for example, performing delay add processing on the signals of the respective elements.

Here, the operations of the transmitting unit 102 and the receiving unit 103 are controlled by a transmission and reception control unit 104. More specifically, for the transmitting unit 102, the transmission and reception control unit 104 switches between driving voltages, set a transmission frequency and so on for certain scanning. The transmission and reception control unit 104 sets the receiving unit 103 delay time and so on for performing reception beam forming. The reception RF signals are provided to a B-mode processing unit 105, a Doppler processing unit 106 and a strain processing unit 107.

The B-mode processing unit 105 performs, for example, logarithmic amplification and envelope demodulation on the reception RF signals to generate B-mode data (also referred to as a B-mode image) in which the signal intensity is expressed as a brightness level. The B-mode processing unit 105 provides the B-mode data to an image memory 108.

The Doppler processing unit 106 analyzes the frequency domain of the reception RF signals, and calculates, for example, flow rate or movement velocity of tissue based on the Doppler effect caused by blood flow or tissue movement. The Doppler processing unit 106 then provides the calculation result to the image memory 108 as Doppler data.

The strain processing unit 107, for example, calculates the amount of strain of the tissue between two different points, using the movement of a specific portion obtained from the reception RF signals. The strain processing unit 107 then provides the calculation result to the image memory 108 as strain data.

An image processing unit 509 selects data to be displayed from among various types of data stored in the image memory 108, and applies predetermined image processing on the selected data. A display unit 112 displays the processing result.

A positional information obtaining unit 110 and a cross-sectional position identifying unit 111 provide, to the image processing unit 509, positional information of the cross-section necessary for obtaining desired cross-section in the three-dimensional space.

More specifically, the positional information obtaining unit 110 obtains positional information 203 of the ultrasonic probe 101 at the time of ultrasonic image obtainment, based on output signals from a camera, a magnetic sensor, and so on.

The cross-sectional position identifying unit 111 receives the cross-section information 202 indicating the positional information of a cut-out cross-section (hereinafter, referred to as specific cross-section) from a user, and provides the received information to the image processing unit 509.

The image processing unit 509 generates a volume image 206 (volume data) which is a three-dimensional image in which ultrasonic images are mapped into the three-dimensional space. The image processing unit 509 generates a cross-sectional image 605 of the specific cross-section identified by the cross-section information 202, using the volume image 206 mapped into the three-dimensional space based on the positional information 203, FIG. 17 is a block diagram illustrating a processing unit, included in the image processing unit 509, used for generating the cross-sectional image of the specific cross-section. The image processing unit 509 constructs the volume image by mapping the obtained ultrasonic images into the three-dimensional space based on the positional information 203. The three-dimensional space is constructed by fundamental units each referred to as a voxel which corresponds to a pixel in two-dimensional space. For example, dividing a 10×10× 10 cm cube into 1 cm units allows the creation of voxels where each voxel has a volume of 1×1×1 cm, and the entire cube is constructed by 10×10×10 voxel units. For mapping, pixel values of the ultrasonic images are assigned to the nearest voxels.

After the cross-sectional position identifying unit 111 identifies the specific cross-section, the image processing unit 509 performs nearest-neighbor interpolation or bicubic interpolation based on the values of the voxels present near the coordinate positions of the respective pixels in the identified cross-section, to generate the pixel values of the pixels. The following describes the operations of each processing unit.

A frame image input unit 191 obtains an index number 211 of a two-dimensional image such as a B mode image or a Doppler image. A positional information determining unit 192 determines, based on the positional information 203 obtained from a sensor, positional information 212 corresponding to the two-dimensional image having the index number 211. The volume generating unit 199 then maps the two-dimensional image having the index number 211 into the three-dimensional space based on the positional information 212. The mapping is performed on all of the target frames. The constructed volume image is stored in a volume memory 198. The voxel data at the position where no frame image is present is interpolated using the value of nearby voxel data. The volume image, which is mapped into the three-dimensional space using frame images, is generated in such a manner.

A cross-sectional image generating unit 597 generates a cross-sectional image 605 by synthesizing the respective pixel values in the cross-section identified by the cross-section information 202 from the values of the voxels near the pixels, and provides the generated cross-sectional image 605 to the display unit 112. The display data of the volume image 206 is provided from the volume memory 198 to the display unit 112.

As described, the ultrasonic image generating device 500 according to a reference example first constructs a volume image, and then synthesizes images of arbitrary cross-sections using the voxel values within the volume image.

For example, an ultrasonic diagnostic device according to Patent Literature 1 writes echo data into memory addresses on a wave transmission/reception coordinate system that is a coordinate calculated from the position of the probe at the time of measurement, and stores the voxel data in association with the wave transmission/reception coordinate system. Then, a transformation table is generated which indicates the position of the cross-sectional image identified by the user in the wave transmission/reception coordinate system (the cross-section identified in the wave transmission/reception space). The ultrasonic diagnostic device interpolates and generates echo data of the pixels on the cross-sectional image, using the voxel data located at the neighboring addresses.

The quality of the specific cross-sectional image generated by such an ultrasonic image generating device depends on the quality of the volume image generated based on the voxel data. Thus, the volume image needs to have high-resolution. In Patent Literature 1, however, no consideration has been made as to a point that the frame images, used for generating the volume image, have different resolution depending on the scanning direction of the ultrasonic probe.

A description is given of the direction dependency of the resolution.

Figure 18A:
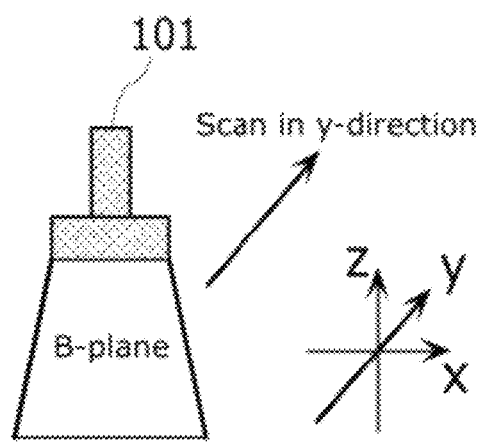
FIG. 18A is a diagram illustrating an example of scanning using the ultrasonic probe.
Figure 18B:
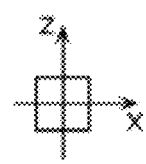
FIG. 18B is a diagram illustrating resolution of the x-z plane when scanning is performed using the ultrasonic probe in the y-axis direction.
Figure 18C:
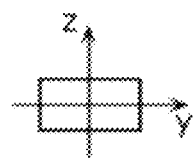
FIG. 18C is a diagram illustrating resolution of the y-z plane when scanning is performed using the ultrasonic probe in the y-axis direction.
Figure 18D:
FIG. 18D is a diagram illustrating a cubic shape that is a target object.

FIG. 18A to FIG. 18H are diagrams for describing the direction dependency of the resolution. FIG. 18A is a diagram illustrating a state where the ultrasonic probe 101 is scanned in y-direction. FIG. 18B and FIG. 18C illustrate resolution of respective planes when the ultrasonic probe 101 is scanned in the y-direction. FIG. 18B illustrates the resolution of the x-z plane which is perpendicular to the scanning direction. FIG. 18C illustrates the resolution of the y-z plane which is parallel to the scanning direction.

As shown in FIG. 18C, the resolution decreases in the scanning direction (y-direction in FIG. 18C) in the plane parallel to the scanning direction (hereinafter, referred to as C-plane). This is because the region of propagation of ultrasonic waves in a medium expands relative to the scanning direction. This phenomenon occurs when the ultrasonic probe has at least one transducer. Such a phenomenon is particularly noticeable in an ultrasonic probe including at least one row of ultrasonic transducers, because it is not possible to focus ultrasonic beams by adding phase differences to ultrasonic waves emitted from the transducers arranged in the scanning direction. It is assumed here that the array direction of the ultrasonic transducers is substantially perpendicular to the scanning direction of the ultrasonic probe.

Figure 18E:
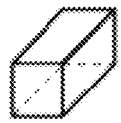
FIG. 18E is a diagram illustrating a volume image.

The resolution of the plane (hereinafter, referred to as B-plane) perpendicular to the scanning direction of the ultrasonic probe and parallel to the array direction of the ultrasonic transducers is higher than that of the C-plane. FIG. 18E illustrates a volume image generated by reflected waves of the ultrasonic waves emitted to a cubic target object shown in FIG. 18D. Since the resolution of the y-axis direction is decreased, the resultant has a rectangle-shape which extends in the y-axis direction as shown in FIG. 18E.

Figure 18F:
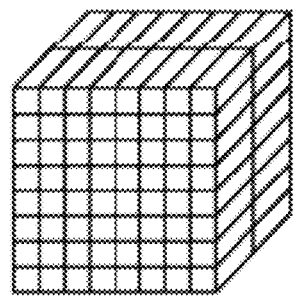
FIG. 18F is a diagram illustrating resolution in a three-dimensional space.
Figure 18G:
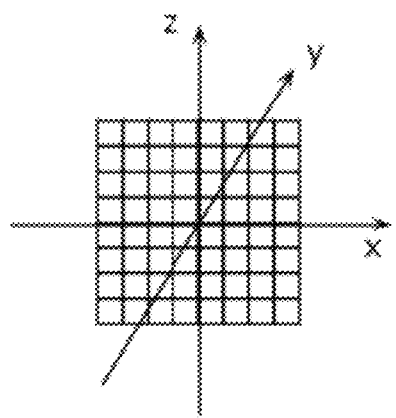
FIG. 18G is a diagram illustrating resolution in the y-z plane.
Figure 18H:
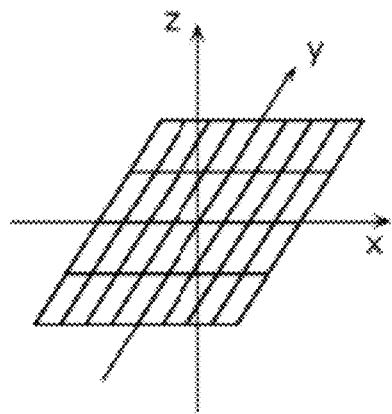
FIG. 18H is a diagram illustrating resolution in the x-y plane.

FIG. 18F, FIG. 18G, and FIG. 18H each illustrates direction dependency of the ultrasonic images presented in the three-dimensional space. FIG. 18F illustrates the resolution in the three-dimensional space. FIG. 18G illustrates the resolution in the x-z plane. FIG. 18H illustrates the resolution in the x-y plane.

The square in the drawing is the minimum unit that can show up on the image on the x-z plane. The rectangle in the drawing is the minimum unit that can show up on the image on the y-z plane. Therefore, the minimum resolution of the ultrasonic probe in the scanning direction is lower than the minimum resolution in the direction perpendicular to the scanning direction.

A description is given of the phenomenon using another example.

FIG. 19A to FIG. 19F each illustrates a volume mage constructed based on the ultrasonic images generated by scanning the target object from different directions. Referring to these drawings, a description is given of the problems caused when arbitrary cross-section images are synthesized from the volume image.

Figure 19A:
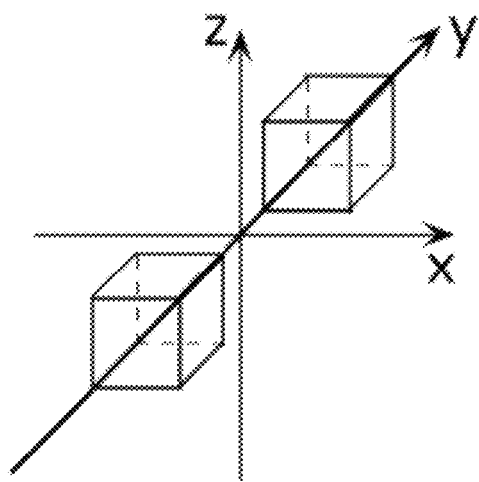
FIG. 19A is a diagram illustrating target objects to which ultrasonic waves are emitted.
Figure 19B:
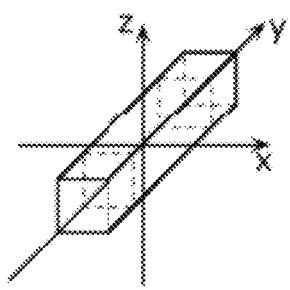
FIG. 19B is a diagram illustrating a volume image obtained when scanning is performed using the ultrasonic probe in the y-axis direction.
Figure 19C:
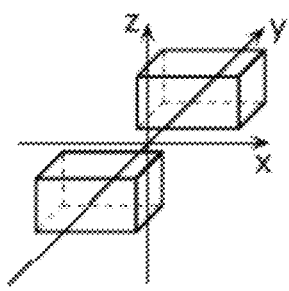
FIG. 19C is a diagram illustrating volume images obtained when scanning is performed using the ultrasonic probe in the x-axis direction.

FIG. 19A illustrates target objects to which ultrasonic waves are emitted. Along the y-axis, two cubes are arranged. FIG. 19B illustrates a resultant image generated by using reflected signals obtained by scanning the target objects along the y-axis direction using the ultrasonic probe. FIG. 19C illustrates a resultant image generated by using the reflected signals obtained by scanning the target objects along the x-axis direction using the ultrasonic probe.

Figure 19D:
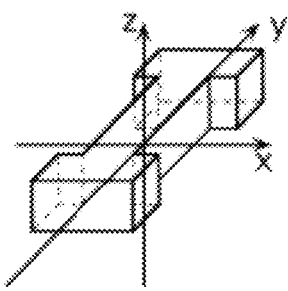
FIG. 19D is a diagram illustrating a volume image obtained by the combining.

For volume image construction, resultant of scanning from different directions are combined. In this example, the image shown in FIG. 19B is combined with the image shown in FIG. 19C. FIG. 19D illustrates a volume image obtained by the combining. The volume image has a decreased resolution because the images having decreased resolution in the scanning direction are combined. Thus, although the target objects are actually two separate objects, they cannot be shown separately in the volume image.

When an arbitrary cross-sectional image is generated from the volume image, the cross-sectional image is cut out from the volume image shown in FIG. 19D.

Figure 19E:
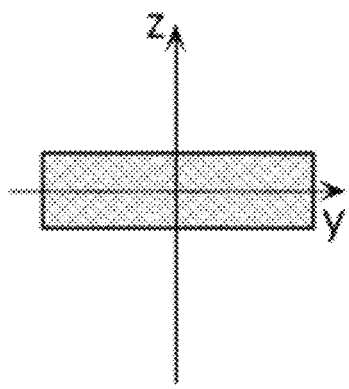
FIG. 19E is a diagram illustrating a cross-sectional mage cut out from the volume image.
Figure 19F:
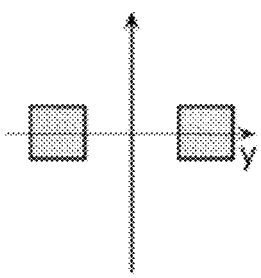
FIG. 19F is a diagram illustrating a correct cross-sectional image.

FIG. 19E illustrates an image of the cross-section parallel to the y-z plane and cut out from the volume image in FIG. 19D. The image, of course, does not show the two target objects separately, but shows one rectangle in which the two target objects are combined. FIG. 19F illustrates a correct cross-sectional image at the position same as FIG. 19E.

As described, the ultrasonic image generating device according to a reference example generates a volume image using ultrasonic images obtained by scanning from different directions using a ultrasonic probe, and then generates cross-sectional images of arbitrary cross-sections using the volume image. Therefore, even though the target objects can be separated on the y-z plane shown in FIG. 19C, a correct cross-sectional image may not be generated as shown in FIG. 19E. In such a manner, the cross-sectional images obtained by the ultrasonic image generating device according to a reference example are synthesized from the volume image constructed without considering the direction dependency of the resolution of the ultrasonic images. Therefore, the ultrasonic image generating device according to a reference example has a degraded accuracy due to the influence of the decreased resolution in the C-plane direction.

One non-limiting and exemplary embodiment provides an ultrasonic image generating device with an increased accuracy.

In one general aspect, the techniques disclosed here feature an ultrasonic image generating device which generates a cross-sectional image of a specific cross-section of a subject from a plurality of ultrasonic images obtained by scanning the subject from a plurality of directions using an ultrasonic probe, and includes: a cross-section position identifying unit which obtains cross-section information indicating a position and an orientation of the specific cross-section; a positional information obtaining unit which obtains positional information including a position and an orientation of each of the ultrasonic images of the subject; a reference image selecting unit which selects at least one of the ultrasonic images as a reference image, the at least one of the ultrasonic images having a distance from the specific cross-section that is less than a first threshold and an orientation difference from the specific cross-section that is less than a second threshold; and a cross-sectional image generating unit which generates the cross-sectional image using the reference image.

With this configuration, the ultrasonic image generating device according to an exemplary embodiment disclosed herein generates cross-sectional images using ultrasonic images each having small orientation difference from a specific cross-section. As a result, the ultrasonic image generating device can generate cross-sectional images using high-resolution ultrasonic images, thereby increasing accuracy of the cross-sectional images.

It also may be that the specific cross-section includes a region of interest, and the reference image selecting unit selects, as the reference image, an ultrasonic image having a distance from a point included in the region of interest in the specific cross-section that is less than the first threshold and an orientation difference from the specific cross-section that is less than the second threshold.

With this configuration, the ultrasonic image generating device according to an exemplary embodiment disclosed herein can increase the accuracy of the region of interest that is particularly important.

It also may be that the reference image selecting unit selects an ultrasonic image as the reference image from the ultrasonic images, for each of a plurality of regions obtained by dividing the specific cross-section, the ultrasonic image having a distance from the region that is less than the first threshold and an orientation difference from the specific cross-section that is less than the second threshold, and the cross-sectional image generating unit generates an image of each of the regions using the reference image selected for the region.

With this configuration, the ultrasonic image generating device according to an exemplary embodiment disclosed herein can increase the accuracy of the cross-sectional images by selecting reference images for respective regions included in the specific cross-sections.

It also may be that the reference image selecting unit selects an ultrasonic image as the reference image from the ultrasonic images for each of the regions, the ultrasonic image having a distance from a central point of the region that is less than the first threshold and an orientation difference from the specific cross-section that is less than the second threshold.

It also may be that the positional information obtaining unit obtains a position and an orientation of the ultrasonic probe to calculate the positional information based on the position and the orientation of the ultrasonic probe.

It may also be that the positional information obtaining unit further obtains a direction of ultrasonic waves emitted from the ultrasonic probe to calculate the positional information based on the direction of the ultrasonic waves and the position and the orientation of the ultrasonic probe.

With this configuration, the ultrasonic image generating device according to an exemplary embodiment disclosed herein can obtain the positional information of the ultrasonic images generated by using, for example, a three-dimensional vibrating probe.

It also may be that the first threshold is less than or equal to a resolution in a C-plane that is parallel to a scanning direction of the ultrasonic probe, and the second threshold is less than or equal to 30 degrees.

With this configuration, the ultrasonic image generating device according to an exemplary embodiment disclosed herein can increase the accuracy of the cross-sectional images.

It may also be that when the ultrasonic images do not include the ultrasonic image having a distance from the specific cross-section that is less than the first threshold and an orientation difference from the specific cross-section that is less than the second threshold, the cross-sectional image generating unit generates the cross-sectional image using an ultrasonic image which is included in the ultrasonic images and has a smallest distance from the specific cross-section.

With this configuration, the ultrasonic image generating device according to an exemplary embodiment disclosed herein can generate cross-sectional images even when no ultrasonic image meets the conditions for the reference images.

It may also be that a volume generating unit generates a volume image from the ultrasonic images, wherein the cross-section position identifying unit generates the cross-section information indicating the specific cross-section identified by a user with respect to the volume image.

The configuration allows a user to easily select specific cross-sections.

It may also be that the reference image selecting unit (i) selects, as the reference image, an ultrasonic image having a distance from the specific cross-section that is less than the first threshold and an orientation difference from the specific cross-section that is less than the second threshold, when the specific cross-section includes a region of interest, and (ii) selects the reference image based only on the distance from the specific cross-section out of the distance from the specific cross-section and the orientation difference from the specific cross-section, when the specific cross-section does not include the region of interest.

With the configuration, the ultrasonic image generating device according to an exemplary embodiment disclosed herein can increase the accuracy of the region of interest which is particularly important, and also can reduce calculation amount relative to less important portions.

It may also be that the reference image includes a plurality of reference images, and the cross-sectional image generating unit (i) generates a pixel value of a pixel included in the cross-sectional image by multiplying a pixel value of a pixel included in each of the reference images by a weighting coefficient and summing resulting pixel values, and (ii) increases the weighting coefficient for a reference image having a smaller orientation difference from the specific cross-section among the reference images.

With this configuration, the ultrasonic image generating device according to an exemplary embodiment disclosed herein can increase the accuracy of the cross-sectional images by using a plurality of reference images.

It may also be that the cross-sectional image generating unit increases the weighting coefficient for a reference image having a smaller orientation difference from the specific cross-section, the reference image being included in the reference images and having a distance from the specific cross-section that is less than a third threshold.

Moreover, the ultrasonic image generating device according to an exemplary embodiment disclosed herein generates a cross-sectional image from a plurality of Doppler images each of which indicates blood flow, the cross-sectional image indicating blood flow in a specific cross-section of a subject, the Doppler images being obtained by scanning the subject from a plurality of directions using an ultrasonic probe. The ultrasonic image generating device includes: a cross-section position identifying unit which obtains cross-section information indicating a position and an orientation of the specific cross-section; a blood flow direction obtaining unit which obtains blood flow information indicating a direction of the blood flow in the specific cross-section; a positional information obtaining unit which obtains positional information including a position and an orientation of each of the Doppler images of the subject; a reference image selecting unit which selects at least one of the Doppler images as a reference image, the at least one of the Doppler images having a distance from the specific cross-section that is less than a first threshold and an orientation different from the direction of the blood flow by less than a second threshold; and a cross-sectional image generating unit which generates the cross-sectional image using the reference image.

With this configuration, the ultrasonic image generating device according to an exemplary embodiment disclosed herein generates cross-sectional images using ultrasonic images each having a small orientation difference from the direction of the blood flow. With this configuration, the ultrasonic image generating device can generate cross-sectional images using highly sensitive Doppler images, thereby increasing the accuracy of the cross-sectional images.

These general and specific aspects may be implemented not only as an ultrasonic image generating device, but also as an image generating method which includes characteristic units as steps, or as a problem causing a computer to execute the steps. Needless to say, such a program may be distributed over a computer-readable nonvolatile recording medium such as a compact disc-read only memory (CD-ROM) or a transmission medium such as the Internet.

Furthermore, these general and specific aspects may be implemented as a semiconductor integrated circuit (LSI) which includes part or all of the functions of the ultrasonic image generating device, or may be implemented as an ultrasonic diagnostic device including the ultrasonic image generating device.

Hereinafter, certain exemplary embodiments are described with reference to the accompanying drawings. Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the scope of the appended Claims and their equivalents. Therefore, among the structural elements in the following exemplary embodiments, structural elements not recited in any one of the independent claims are described as arbitrary structural elements.

Embodiment 1

An ultrasonic image generating device according to Embodiment 1 disclosed herein generates cross-sectional images from original ultrasonic images instead of generating cross-sectional images from a volume image. In addition, the ultrasonic image generating device determines reference images used for generating the cross-sectional images, based on the distance between the cross-sectional image and the ultrasonic image, and the orientations of the cross-sectional image and the ultrasonic image. As a result, the ultrasonic image generating device according to Embodiment 1 disclosed herein increases accuracy of the cross-sectional images.

Figure 1:
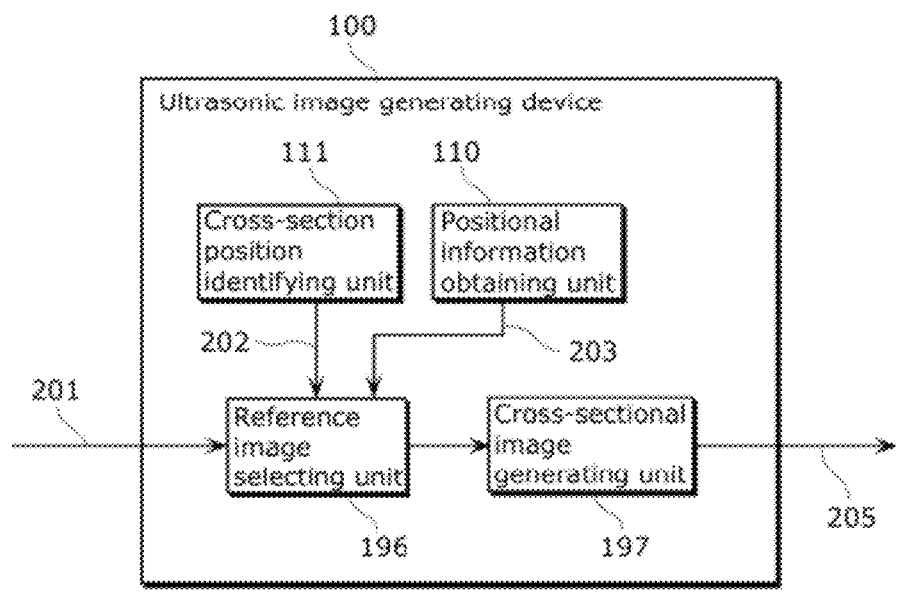
FIG. 1 is a block diagram of an ultrasonic image generating device according to Embodiment 1.

First, a description is given of a basic configuration of the ultrasonic image generating device according to Embodiment 1 disclosed herein. FIG. 1 is a block diagram of an ultrasonic image generating device 100 according to Embodiment 1.

The ultrasonic image generating device 100 shown in FIG. 1 generates a cross-sectional image 205 of a specific cross-section of a subject from a plurality of ultrasonic images 201 obtained by scanning the subject from different directions using an ultrasonic probe 101. The ultrasonic image generating device 100 includes: a cross-section position identifying unit 111; a positional information obtaining unit 110; a reference image selecting unit 196; and a cross-sectional image generating unit 197.

The cross-sectional position identifying unit 111 obtains cross-section information 202 indicating the position and the orientation of the specific cross-section.

The positional information obtaining unit 110 obtains positional information 203 including respective positions and orientations of the ultrasonic images 201 of the subject. More specifically, the positional information obtaining unit 110 obtains, as the positional information 203, probe positional information (the position and the orientation of the ultrasonic probe 101) at the time of obtainment of the ultrasonic images detected by a position sensor such as a camera or a magnetic sensor. The positional information obtaining unit 110 may calculate the positional information 203 using the probe positional information. The orientation of the ultrasonic probe 101 is the orientation of the plane which is along the direction of the ultrasonic waves emitted by the ultrasonic probe 101 and which is parallel to the array direction of the ultrasonic transducers. In other words, the orientation of the ultrasonic probe 101 is the orientation of the B-plane.

The reference image selecting unit 196 selects at least one ultrasonic image 201 from the ultrasonic images 201 as a reference image. The selected ultrasonic image 201 has a distance from the specific cross-section that is less than a first threshold, and an orientation difference from the specific cross-section that is less than a second threshold.

The cross-sectional image generating unit 197 generates the cross-sectional image 205 using the reference images selected by the reference image selecting unit 196.

Figure 2A:
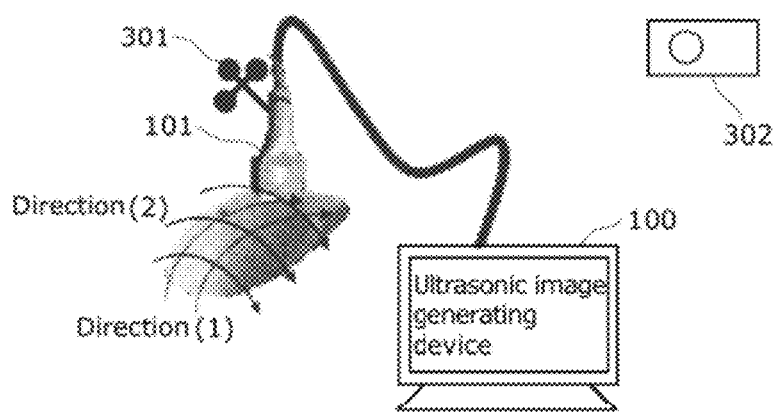
FIG. 2A illustrates a use example of the ultrasonic image generating device according to Embodiment 1.

Hereinafter, descriptions are given of the ultrasonic image generating device 100 and an image generating method according to Embodiment 1, with reference to the drawings. In the following, a general description is given of the functions of the ultrasonic image generating device 100, with an example of breast examination. FIG. 2A is a diagram showing a usage example of the ultrasonic image generating device 100.

As shown in FIG. 2A, the ultrasonic image generating device 100 obtains ultrasonic images 201 of a breast taken from different directions, by scanning the breast using the ultrasonic probe 101 from different directions such as direction (1) and direction (2). Examples of the ultrasonic probe 101 that may be used include a linear array probe, a three-dimensional (3D) vibrating probe, and a matrix array probe. The linear array probe includes at least one row of ultrasonic transducers, and provides two-dimensional images. The 3D vibrating probe includes one row of ultrasonic transducers, and continuously generates two-dimensional images by the vibration or linear movement of the ultrasonic transducers. The 3D vibrating probe provides three-dimensional images by using the two-dimensional images thus generated. The matrix array probe includes transducers that are two-dimensionally arranged, and provides three dimensional images. In Embodiment 1, a description is given of an example where the linear array probe is used.

The ultrasonic probe 101 is equipped with an optical marker 301. A camera 302 captures images of the optical marker 301. The ultrasonic image generating device 100 analyzes the changes of the position and the posture of the optical marker 301 by using the images captured by the camera 302, to obtain the positional information of the ultrasonic probe 101 (hereinafter, referred to as probe positional information) at the time of obtainment of the ultrasonic signals used for the ultrasonic image generating device 100 to generate the ultrasonic images 201. Hereinafter, the time when the ultrasonic image generating device 100 obtains the ultrasonic signals for generating the ultrasonic images 201 is referred to as obtainment timing of the ultrasonic images 201.

The ultrasonic probe 101 and the camera 302 operate in synchronization with one another, or operate according to respective known reference clocks, to match the obtainment timing of the ultrasonic images 201 and the obtainment timing of the positional information 203. The probe positional information indicates the position and the orientation of the ultrasonic probe 101. More specifically, the probe positional information includes six parameters in total which are the positions (corresponds to coordinate values of x, y, and z axes) and orientations (rotation about three respective axes) in the three-dimensional space.

FIG. 2A shows an example where the optical marker 301 is attached to the ultrasonic probe 101; however, it may be that the camera 302 is attached to the ultrasonic probe 101 and the optical marker 301 is arranged around the ultrasonic probe 101. In this case, it is desirable to use a plurality of optical markers 301 in order to increase the accuracy of the position detection.

Figure 2B:
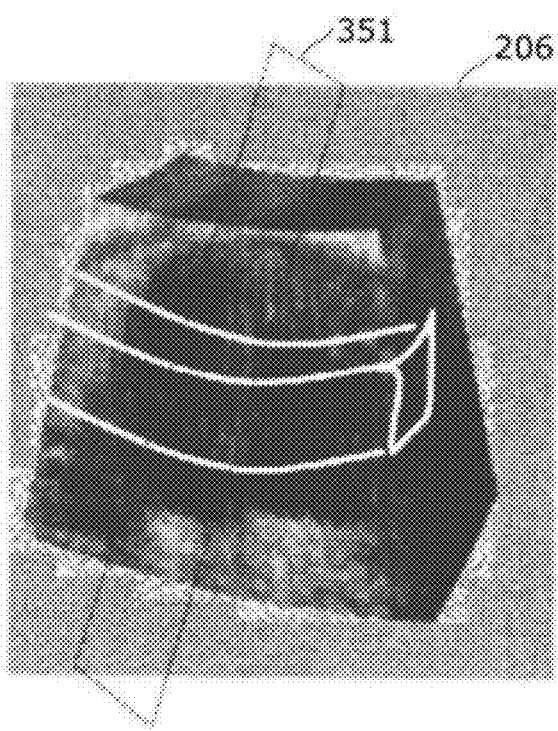
FIG. 2B is a diagram illustrating a volume image obtained by the ultrasonic image generating device according to Embodiment 1.
Figure 2C:
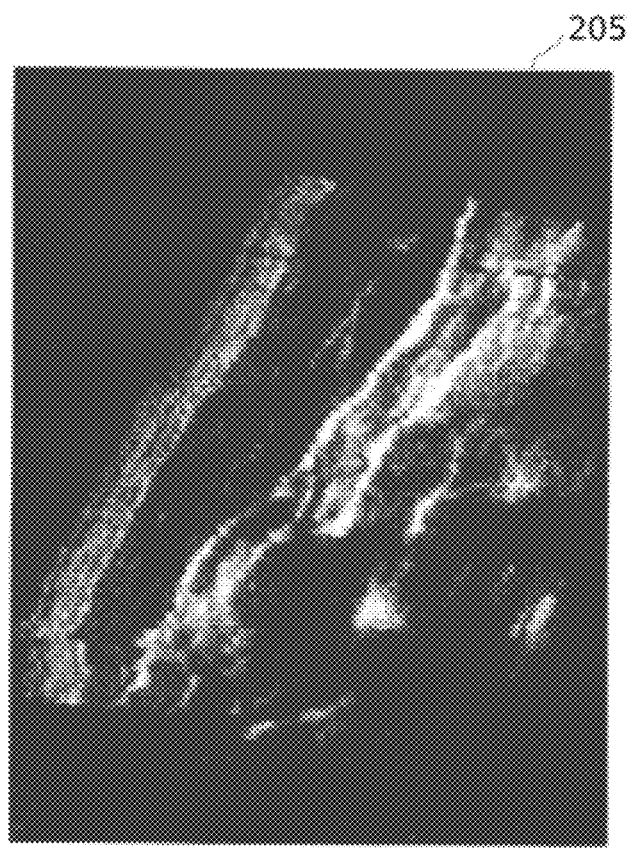
FIG. 2C illustrates a cross-sectional image obtained by the ultrasonic image generating device according to Embodiment 1.

FIG. 2B is a volume image 206 of the inside the breast shown in FIG. 2A. When a user identifies a specific cross-section 351 surrounded with a dotted line in FIG. 2B, via, for example, a user interface on the display, the cross-sectional image 205 of the specific cross-section 351 is generated to be displayed on the display screen of the ultrasonic image generating device 100, as shown in FIG. 2C.

Figure 3:
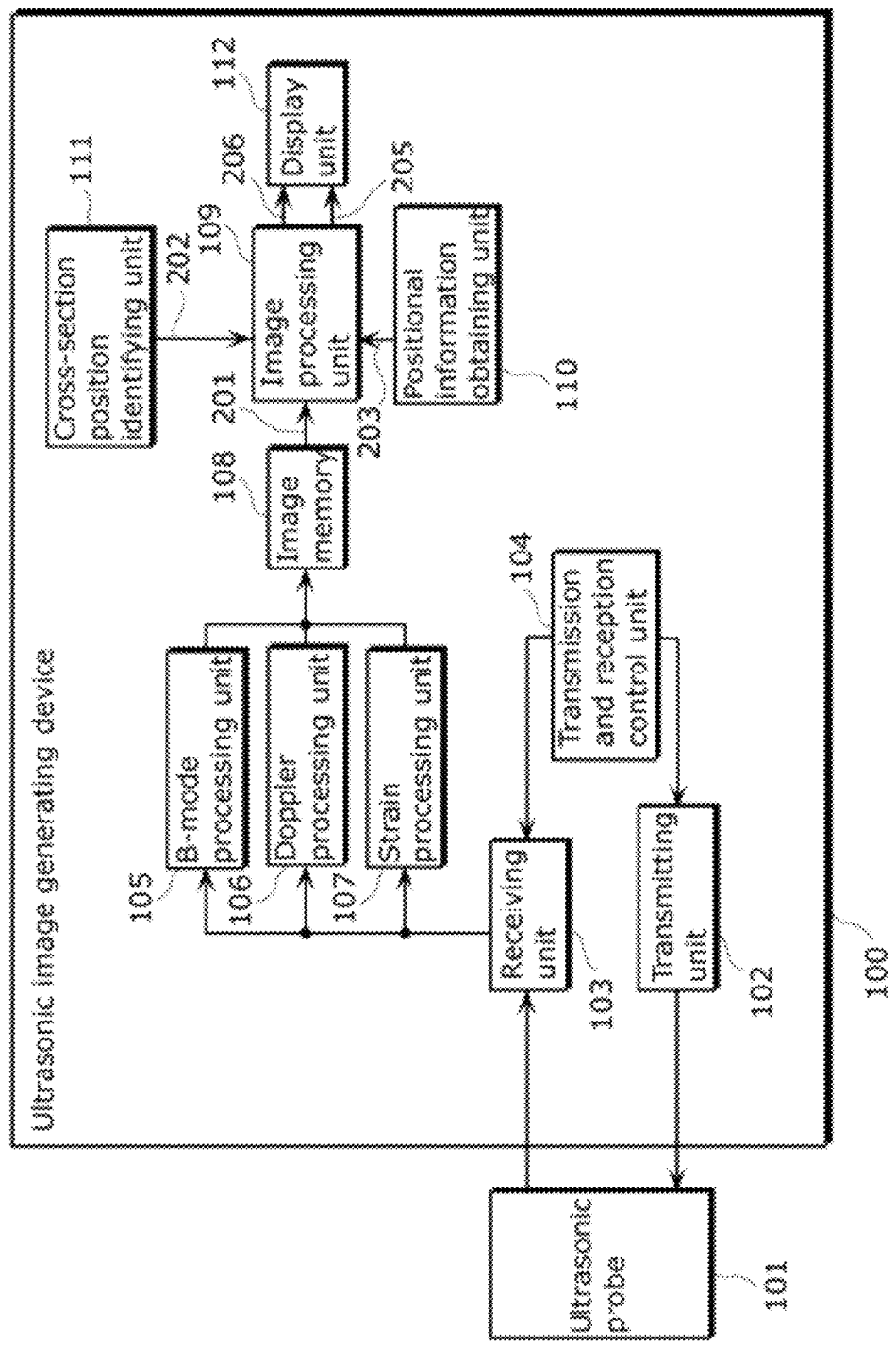
FIG. 3 is a block diagram illustrating a configuration of the ultrasonic image generating device according to Embodiment 1.

FIG. 3 is a block diagram of a configuration of the ultrasonic image generating device 100 according to Embodiment 1. The ultrasonic image generating device 100 includes the ultrasonic probe 101, a transmitting unit 102, a receiving unit 103, a transmission and reception control unit 104, a B-mode processing unit 105, a Doppler processing unit 106, a strain processing unit 107, an image memory 108, an image processing unit 109, a positional information obtaining unit 110, a cross-sectional position identifying unit 111, and a display unit 112.

The ultrasonic image generating device 100 according to Embodiment 1 has features in the operations of the image processing unit 109. Thus, the operations of the image processing unit 109 will be mainly described in the following, and descriptions of the other processing units may be omitted. The operations of the respective processing units which receive and transmit ultrasonic signals and perform B-mode processing or Doppler processing are the same as those of the ultrasonic image generating device 500 according to a reference example. In addition, the same referential numbers are assigned to the elements similar to those of FIG. 16.

FIG. 3 illustrates the B-mode processing unit 105, the Doppler processing unit 106, and the strain processing unit 107 as units for processing ultrasonic signals provided from the receiving unit 103 which receives the ultrasonic signals. However, such configurations are not essential for the ultrasonic image generating device 100. It is sufficient that the ultrasonic image generating device 100 includes at least one of the B-mode processing unit 105, the Doppler processing unit 106, and the strain processing unit 107, depending on the types of the images to be displayed on the display unit 112. It may also be that the ultrasonic image generating device 100 does not include the display unit 112, and the ultrasonic image generating device 100 provides display images to the display unit 112 provided externally.

Furthermore, in Embodiment 1, data which indicates an image or volume image is simply referred to as an image and a volume image.

Figure 4:
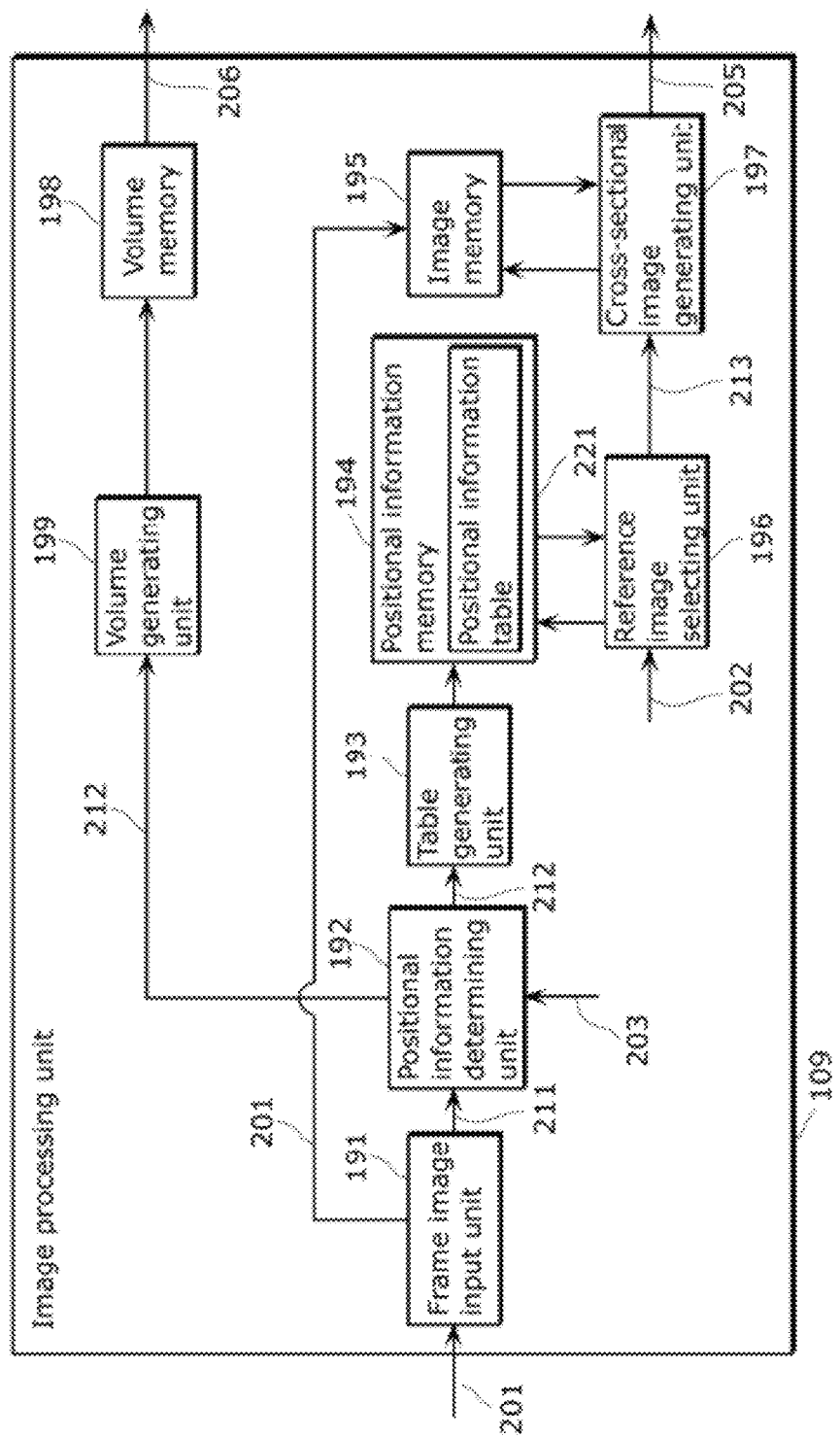
FIG. 4 is a block diagram illustrating a configuration of an image processing unit according to Embodiment 1.

FIG. 4 is a block diagram illustrating a configuration of the image processing unit 109. The image processing unit 109 includes a frame image input unit 191, a positional information determining unit 192, a table generating unit 193, a positional information memory 194, an image memory 195, a reference image selecting unit 196, and a cross-sectional image generating unit 197.

The frame image input unit 191 obtains ultrasonic images 201 that are two-dimensional images, such as B-mode images or Doppler images, stored in the image memory 108, and index numbers 211 of the ultrasonic images 201. The index numbers 211 are associated with, for example, the ultrasonic images 201. The index numbers 211 are stored in the image memory 108 with the ultrasonic images 201. The frame image input unit 191 stores the obtained ultrasonic images 201 and index numbers 211 into the image memory 195, and provides the index numbers 211 to the positional information determining unit 192. In the following, a description is given of an example where the ultrasonic images 201 are B-mode images.

The positional information determining unit 192 determines the positional information 212 corresponds to the ultrasonic image 201 having the index number 211 based on the positional information 203 obtained by the positional information obtaining unit 110. The positional information 203 and 212 indicate the position and the orientation of a specific part of the optical marker 301 attached to the ultrasonic probe 101 or the ultrasonic probe 101 relative to a known normal coordinate. It may be that the image processing unit 109 does not include the frame image input unit 191, but the table generating unit 193 assigns index numbers to respective images.

Next, the table generating unit 193 associates the positional information 212 of each ultrasonic image 201 (frame) with the index number 211 of each ultrasonic image 201 based on the positional information 212, and generates a positional information table 221 indicating the association. The positional information memory 194 stores the positional information table 221 generated by the table generating unit 193. The positional information memory 194 does not have to store the association as a table as long as the positional information memory 194 stores the positional information 212 of the ultrasonic image 201 in association with the index number 211 of the ultrasonic image 201. The positional information in the positional information memory 194 may be the same as the positional information 212, and also may be values transformed into different coordinate systems. One example of the different coordinate systems is a three-dimensional coordinate system used by the image processing unit 109 or the display unit 112.

The reference image selecting unit 196 determines frames (hereinafter, referred to as reference images) to be referred to for synthesizing respective pixel values of the cross-sectional image 205, with reference to the positional information table 221. The reference image selecting unit 196 provides, to the cross-sectional image generating unit 197, the index numbers of the determined reference images as reference image information 213.

The cross-sectional image generating unit 197 obtains the reference images indicated by the reference image information 213 from the image memory 195. The cross-sectional image generating unit 197 then adaptively applies weighting to pixels in the reference images and combining pixel values to generate the cross-sectional image 205. The cross-sectional image generating unit 197 provides the generated cross-sectional image 205 to the display unit 112.

For displaying the volume image 206 on the display unit 112, the image processing unit 109 may additionally include a volume generating unit 199 and a volume memory 198. In other words, the image processing unit 109 does not have to include the volume generating unit 199 and the volume memory 198.

The volume generating unit 199 constructs the volume image 206 based on the positional information 203 and the ultrasonic images 201, and stores the volume image 206 in the volume memory 198. The display unit 112 then obtains the volume image 206 from the volume memory 198, and displays the obtained volume image 206.

When a user identifies the specific cross-section 351 with respect to the displayed volume image 206, the cross-sectional position identifying unit 111 generates the cross-section information 202 indicating the position and the orientation of the specific cross-section 351. The cross-sectional image generating unit 197 then generates respective pixel values of the specific cross-section 351 indicated by the cross-section information 202, using the reference images selected by the reference image selecting unit 196.

Figure 5:
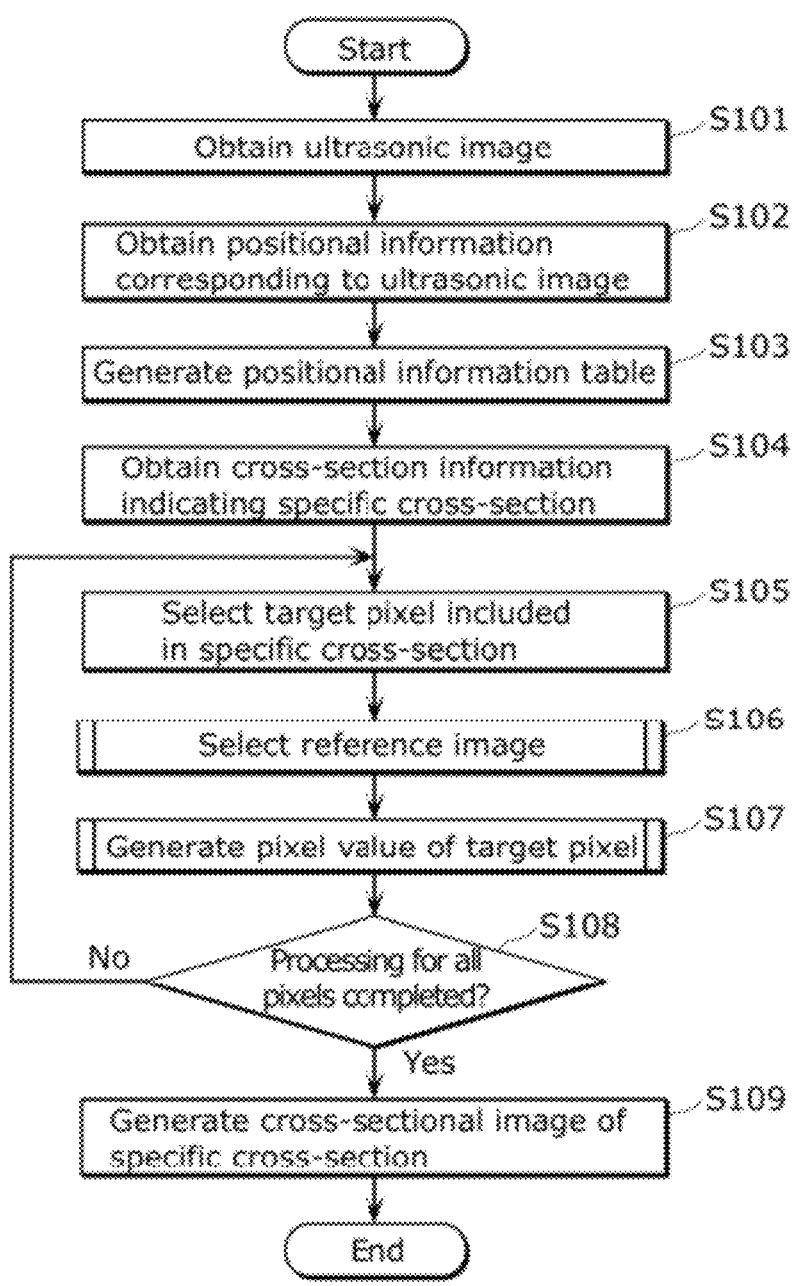
FIG. 5 is a flowchart of processing for generating an image of a specific cross-section according to Embodiment 1.

FIG. 5 is a flowchart of processing for synthesizing cross-sectional images performed by each processing unit of the image processing unit 109.

First, the frame image input unit 191 obtains the ultrasonic image 201 generated from the ultrasonic signals obtained by the ultrasonic probe 101 (S101).

Next, the positional information obtaining unit 110 obtains, based on the output signals from the position sensor or the like, the positional information 203 corresponding to the ultrasonic image 201 (S102). Here, when the ultrasonic signals used for generating the ultrasonic image 201 are received, the position and the orientation of the ultrasonic probe 101 are obtained as the positional information 203.

The table generating unit 193 then associates the ultrasonic image 201 and the positional information 203 (212)

and generates the positional information table 221 indicating the association (S103). It may be that the image processing unit 109 does not generate the positional information table 221, but simply add the positional information 203 to each ultrasonic image 201 as index information. It may also be that the obtainment timing of the ultrasonic image 201 does not strictly match the obtainment timing of the positional information 203. For example, the positional information obtaining unit 110 may obtain the positional information 203 immediately after the obtainment of the ultrasonic image 201.

The cross-sectional position identifying unit 111 obtains, for example, the cross-section information 202 indicating the specific cross-section identified by the user (S104).

The image processing unit 109 then generates the pixel values in the specific cross-section identified by the cross-section information 202. This generation processing is performed for each pixel or for each region including a group of pixels (however, the region is smaller than the specific cross-section). The following describes an example where the generation processing is performed for each pixel.

First, the image processing unit 109 selects a pixel to be processed (hereinafter, referred to as a target pixel) included in the specific cross-section (S105).

The reference image selecting unit 196 then calculates the position in the three-dimensional space of the target pixel in the specific cross-section. The reference image selecting unit 196 then selects reference images based on the position of the target pixel and the position of each ultrasonic image 201 (S106). The processing for selecting the reference images will be described later in detail.

The cross-sectional image generating unit 197 then generates (S107) the pixel value of the target pixel using the pixel values of the reference images selected in Step S106. The details of the processing will be described later.

In the case where the processing of Steps S105 to S107 have not been completed for all of the pixels in the specific cross-section (NO in S108), a new target pixel is selected in Step S105, and the processing after Step S106 is performed on the selected target pixel.

In the case where the processing of Steps S105 to S107 have been completed for all of the pixels in the specific cross-section (Yes in S108), the cross-sectional image generating unit 197 generates the cross-sectional image 205 of the specific cross-section, using the pixel value of each pixel generated in the above processing (S109).

Figure 6:
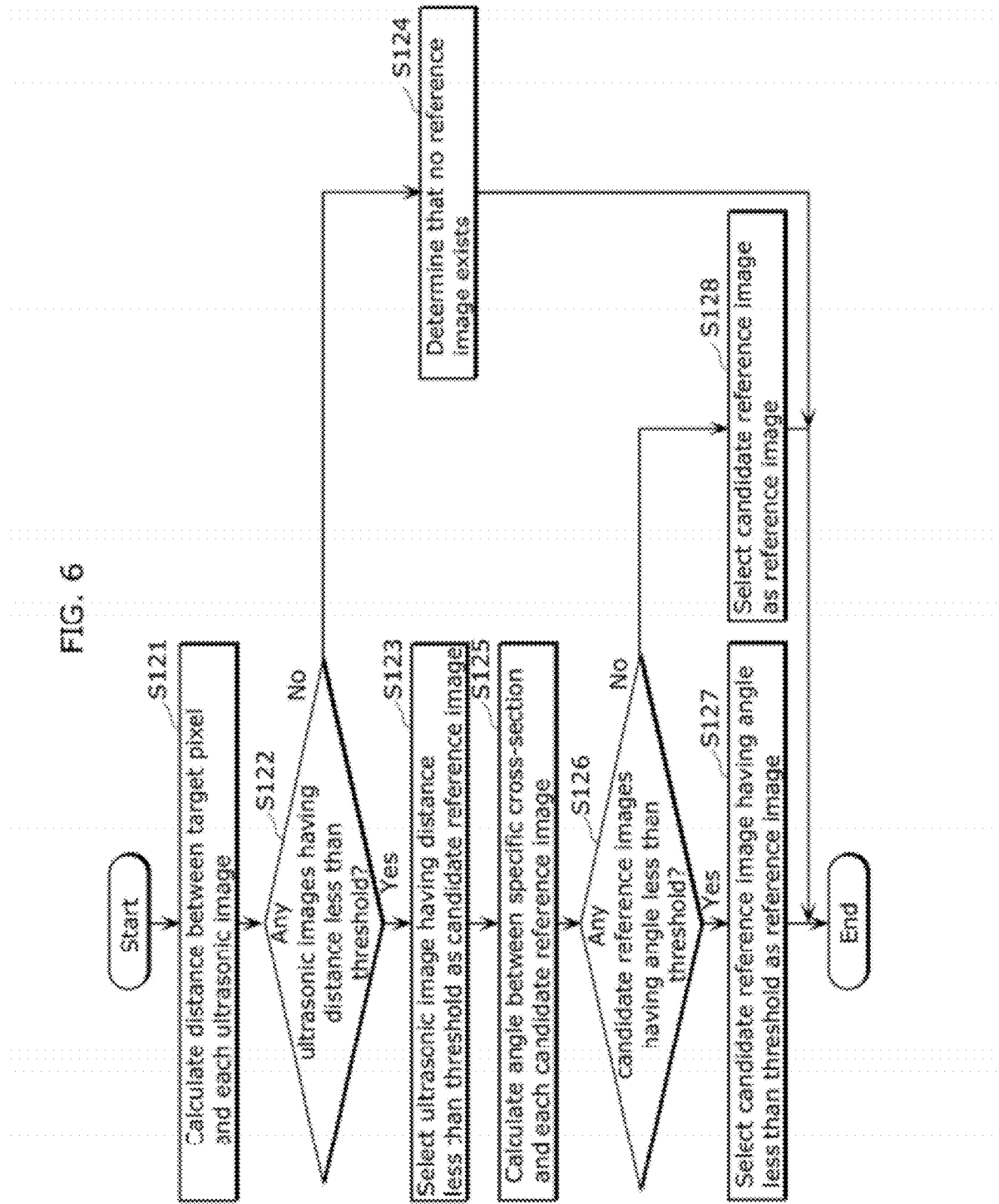
FIG. 6 is a flowchart of processing for selecting reference images according to Embodiment 1.

The following describes the processing for selecting the reference images (S106). FIG. 6 is a flowchart of a detail of the operations of the reference image selecting unit 196.

First, the reference image selecting unit 196 calculates the distance between the target pixel and each ultrasonic image 201 (S121). Next, the reference image selecting unit 196 determines whether or not there are any ultrasonic images 201 having a distance that is less than threshold T1 (S122).

When there are ultrasonic images 201 each having a distance that is less than the threshold T1 (Yes in S122), the reference image selecting unit 196 selects the ultrasonic images 201 as candidate reference images (S123).

Here, it is defined that the distance between the target pixel and the ultrasonic image 201 is the length of a perpendicular line drawn from the target pixel mapped into the three-dimensional space to the ultrasonic image 201. When the processing is performed for each region, the distance is the distance between the target region and the ultrasonic image 201. For example, the distance is the length of a perpendicular line drawn from the central point of the target region to the ultrasonic image 201. When the specific cross-section or the target region includes a region of interest (ROI), the distance may be a distance between a point included in the ROI and the ultrasonic image 201. When a tumor in the specific cross-section is observed, the ROI is a tumor and the neighboring region. The ROI is set by a user, or automatically set by image processing techniques such as boundary extraction or object recognition.

Here, the ultrasonic image 201 used as a reference mage refers to all or part of the frames having index numbers stored in the positional information table 221. It is desirable that the threshold T1 is set to be, for example, smaller than the beam diameter at the position where ultrasonic waves spread least (focus point). It is also desirable that the threshold T1 is set to be a value equal to or less than the resolution in the C-plane at the position of the target pixel. As a result, it is possible to generate higher-resolution images compared to the conventional images.

Next, the reference image selecting unit 196 calculates the angle between the specific cross-section and each candidate reference image (S125). The reference image selecting unit 196 then determines whether or not the candidate reference images include any frames having an orientation difference from the specific cross-section that is less than threshold T2 (S126). Here, it is desirable that the threshold T2 is a value equal to or less than 30 degrees.

When there are candidate reference images each having the orientation difference that is less than the threshold T2 (Yes in S126), the reference image selecting unit 196 selects, as reference images, the candidate reference images having the orientation difference that is less than the threshold T2 (S127).

When there is no candidate reference image having the orientation difference that is less than the threshold T2 (No in S126), the reference image selecting unit 196 selects the candidate reference images determined in S123, as reference images (S128).

When there is no ultrasonic image 201 having the distance that is less than the threshold T1 (No in S122), the reference image selecting unit 196 determines that there is no reference image (S124), and ends searching for the reference images.

It has been described that the reference image selecting unit 196 uses, for determining the reference images, two parameters that are the distance between the target pixel and the ultrasonic image 201 and the orientation difference between the specific cross-section and the ultrasonic image 201; however, other parameters may be combined. The following describes examples of three other parameters that are the movement speed of the ultrasonic probe 101 at the time of obtainment of the ultrasonic images 201, focus positions in the ultrasonic images 201, and frequency distribution in the ultrasonic images 201.

First, a description is given of a case where the movement speed is used. When the movement speed is faster relative to the frame rate at the time of the obtainment of the ultrasonic images 201, the ultrasonic probe 101 moves while the ultrasonic images 201 are being obtained, resulting in so called motion blur. As a result, the resolution of the ultrasonic images 201 decreases. It can be defined that the movement speed of the ultrasonic probe 101 is the movement distance of the ultrasonic probe 101 in a unit time. Thus, the movement speed can be calculated from the interval between neighboring frames and the frame rate.

For determining the reference images, the reference image selecting unit 196 preferentially uses the ultrasonic images 201 having the motion blur within the acceptable range, or the ultrasonic images 201 having the movement speed that is equal to or less than the threshold. In this case, the table generating unit 193 may generate the positional information table 221 including information of the movement speed of the ultrasonic probe 101.

Next, a description is given of a case where the focus position information is added as a condition for determining the reference images. The image quality of the ultrasonic image 201 varies depending on the convergence position of ultrasonic waves emitted from the ultrasonic probe 101. In other words, in the ultrasonic image 201, the depth near the convergence position is in focus, thereby providing high-resolution images. The resolution decreases due to being out of focus, the further the distance from the convergence position is. The reference image selecting unit 196 preferentially selects pixels near the convergence position when reference images are determined from the pixels of the ultrasonic image 201. The convergence position may be obtained as a parameter value of the ultrasonic probe 101 at the time of the obtainment of the ultrasonic image 201. In this case, the positional information table 221 may further include convergence position information. Since the resolution of ultrasonic waves decreases as the depth increases, the depth of the pixels may also be used as a parameter. More specifically, the reference image selecting unit 196 preferentially selects pixels having narrow depth for determining the reference images.

Lastly, a description is given of the case where frequency distribution in the ultrasonic image 201 is added as a condition for determining the reference images. The objective of the selection of the reference images is to select the ultrasonic images 201 having high resolution near a target pixel. The reference image selecting unit 196 performs frequency analysis on the ultrasonic images 201 by, for example, fast Fourier transformation, and preferentially selects, as a reference image, the ultrasonic images 201 including a large amount of high frequency components. In this case, the positional information table 221 may include rate of the high frequency components in each ultrasonic image 201 (for example, average frequency).

In addition, the reference images may be determined in view of continuity of pixels. This is because the result of the combining may be discontinuous when each pixel has a different reference image. Thus, the reference image selecting unit 196 may preferentially select, as a reference image for the target pixel, the reference image selected for a neighboring pixel of the target pixel. More specifically, in the case where a first reference image selected for a target pixel is different from a second reference image used for a neighboring pixel of the target pixel and where the distance or the orientation difference between the first reference image and the second reference image is smaller than a predetermined value, the reference image selecting unit 196 may select the second reference image as a reference image for the target pixel.

Selecting a reference image for each pixel requires a large amount of calculations. In the case where cross-sectional images are displayed while being switched in real-time, it is effective to reduce the amount of calculation. Thus, a reference image may be selected for each specific cross-section or each region within the specific cross-section. Here, the evaluation of the distance and the orientation may be performed for the pixel corresponding to the central point of the specific cross-section or of each region within the specific cross-section.

For observing a tumor within the specific cross-section, the ROI including the tumor and the neighboring region is particularly important. Thus, it may be that the reference image selecting unit 196 selects reference images for the ROI by smaller particle size, such as in a unit of pixel, and select reference images for regions other than the ROI by larger particle size, such as in a unit of region.

In FIG. 6, the reference image selecting unit 196 selects reference images according to the angle after selecting the candidate reference images according to the distance; however, the order may be inverse. Furthermore, some processing may be performed in parallel.

Figure 7:
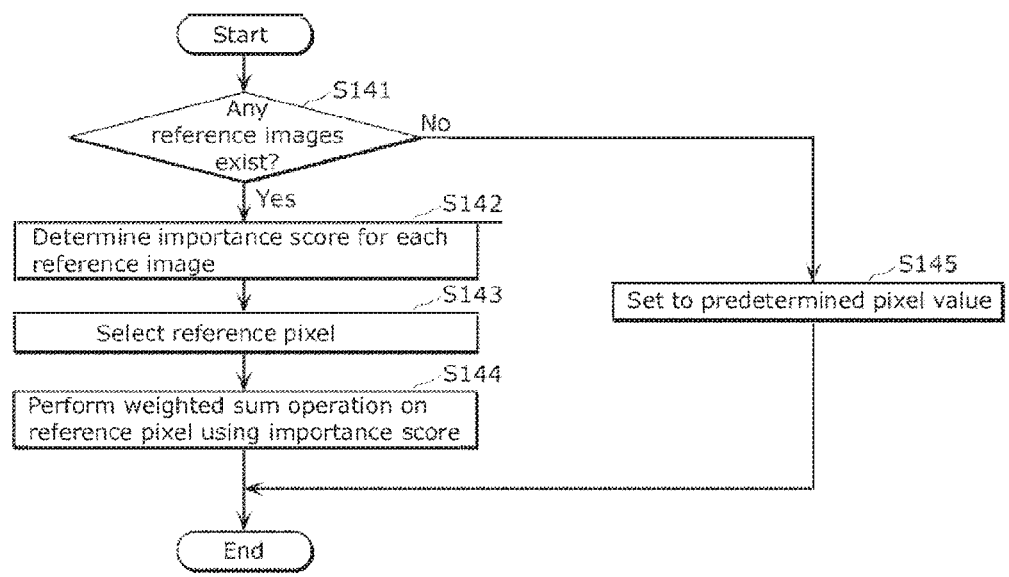
FIG. 7 is a flowchart of processing for generating pixel values of the specific cross-section according to Embodiment 1.

Hereinafter, a detailed description is given of the processing for generating the pixel value of a target pixel (S107). FIG. 7 is a flowchart of the detailed processing for generating the pixel value of the target pixel performed by the cross-sectional image generating unit 197.

First, the cross-sectional image generating unit 197 determines whether or not there are any reference images for a target pixel (S141).

When there are reference images (YES in S141), the cross-sectional image generating unit 197 calculates the importance score of each reference image by performing a weighted sum operation on a first score determined based on the distance between the target pixel and the reference image and on a second score determined based on an orientation difference between the specific cross-section and the reference image (S142) The cross-sectional image generating unit 197 sets the first score and the second score such that the weight of the first score increases as the distance decreases and that the weight of the second score increases as the orientation difference decreases. When the reference images do not include any frames having the orientation difference that is less than the threshold T2, the cross-sectional image generating unit 197 calculates the importance score based only on the first score. For example, the weight of the first score is the same as that of the second score.

When an ultrasonic image obtained near a target position is emphasized, it suffices to increase the weight of the first score (the coefficient by which the first score is multiplied is set to be greater than the coefficient by which the second score is multiplied). When an ultrasonic image that is nearer to the B-plane than to the target pixel is emphasized, it suffices to increase the weight of the second score (the coefficient by which the second score is multiplied is set to be greater than the coefficient by which the first score is multiplied).

Out of the selected reference images and the reference images each having a distance from the target pixel that is less than a third threshold, the weighting coefficient may be increased for a reference image having a smaller orientation difference from the specific cross-section. Here, the third threshold is smaller than the first threshold T1. As a result, it is possible to obtain higher-quality cross-sectional images than ultrasonic images according to a reference example.

Next, the cross-sectional image generating unit 197 selects reference pixels used for generating the target pixel, based on the importance score of each reference image (S143). Lastly, the cross-sectional image generating unit 197 calculates the pixel value of the target pixel by performing weighted sum operation on the pixel values of the reference pixels selected in Step S143 using the importance score of the reference images which include the reference pixels (S144).

When there is no reference image in Step S141 (NO in S141), the cross-sectional image generating unit 197 does not combine the pixel values for the target pixel, but assigns a predetermined pixel value, for example, "0" to the target pixel (S145).

Figure 8:
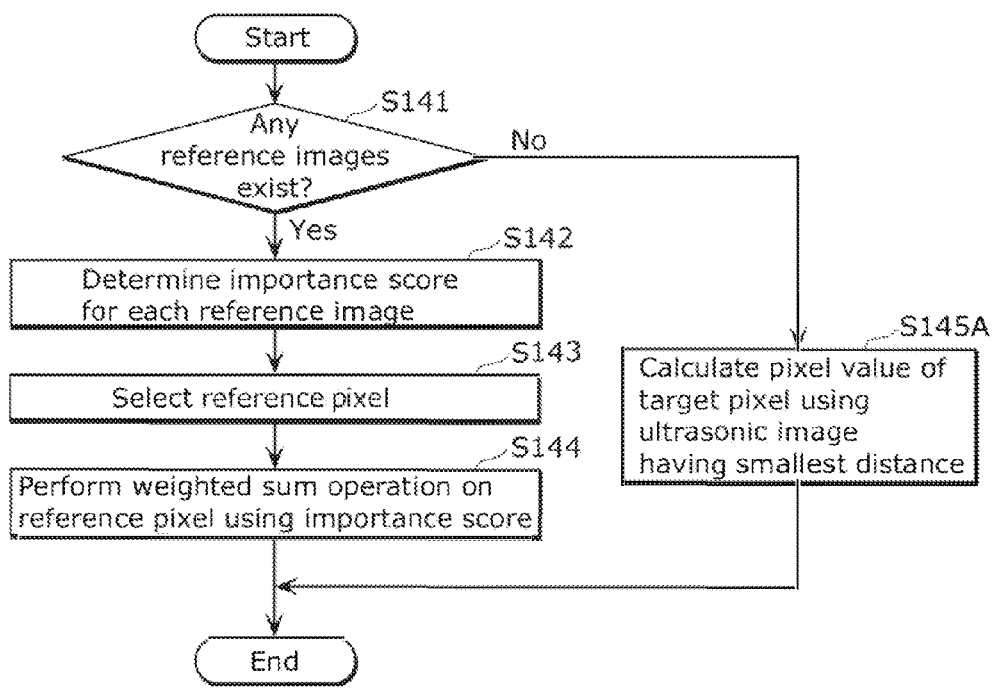
FIG. 8 is a flowchart of a variation of processing for generating pixel values of the specific cross-section according to Embodiment 1.

As shown in FIG. 8, when there is no reference image (NO in S141), the cross-sectional image generating unit 197 may generate a target pixel using the pixel value of the ultrasonic image 201 having smallest distance from the target pixel (S145A).

It may also be that the cross-sectional image generating unit 197 interpolates and generates a target pixel by using the pixel values of the prior calculated pixel located near the target pixel.

Furthermore, the generated cross-sectional image 205 may distinguish the synthesized pixels from the non-synthesized pixels because of absence of the reference images, by, for example, displaying them in different colors.

For performing the combining, at least one pixel of the ultrasonic image 201 needs to be present within a range of the distance from the target pixel that is less than the threshold T1. Thus, some specific cross-sections may include a number of pixels that cannot be synthesized. Therefore, as shown in FIG. 2B, it may be that a volume image constructed from the ultrasonic images 201 is displayed indicating the cross-sections that can be synthesized. In other words, it may be that voxels having the pixels of the ultrasonic image 201 within a range of the distance that is less than the threshold T1 are identified as voxels that can be combined, in order to be distinguished from voxels that cannot be combined. For example, different colors may be used for displaying the voxels that can be combined and the voxels that cannot be combined.

When the specific cross-section is identified by a user, or is automatically set, it is desirable that a specific cross-section is selected with reference to the combinable or uncombinable information such that the specific cross section includes at least two or more pixels that can be synthesized. Alternatively, as a simpler method, a display may be performed such that voxels which include pixels of the ultrasonic images 201 are distinguished from voxels which include no pixel of the ultrasonic images 201.

Furthermore, when the cross-sectional position identifying unit 111 identifies the specific cross-section, the display unit 112 may present, to the user, information indicating which pixel can be synthesized and cannot be synthesized in the specific cross-section. When the rate of the pixels that cannot be synthesized in the specific cross-section or in the ROI in the specific cross-section exceeds a predetermined rate, information may be presented which prompt the user to identify a different neighboring cross-section.

Figure 9A:
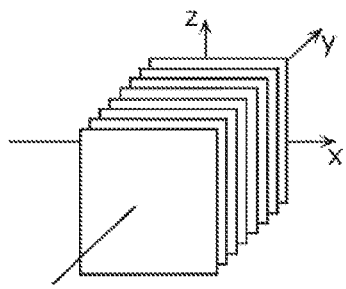
FIG. 9A is a diagram illustrating a group of ultrasonic images obtained when scanning is performed using a ultrasonic probe in the y-axis direction according to Embodiment 1.
Figure 9B:
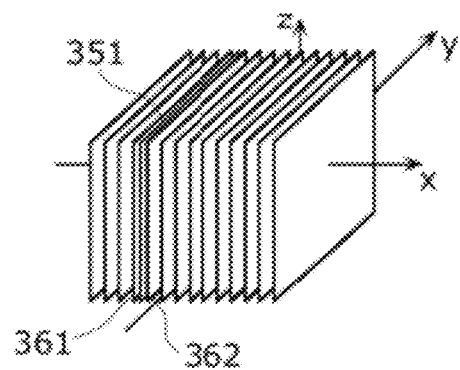
FIG. 9B is a diagram illustrating a group of ultrasonic images obtained when scanning is performed using the ultrasonic probe in the x-axis direction according to Embodiment 1.
Figure 9C:
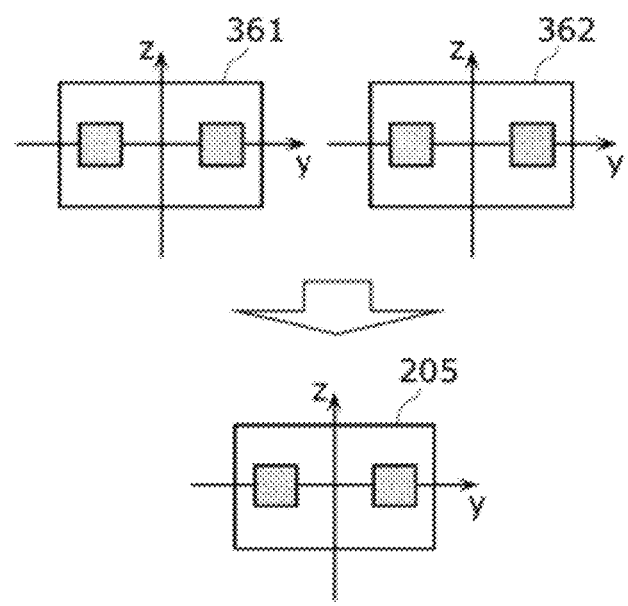
FIG. 9C is a diagram illustrating reference images and a cross-sectional image according to Embodiment 1.

FIG. 9A, FIG. 9B, and FIG. 9C are diagrams for describing the advantageous effects of the ultrasonic image generating device 100 according to Embodiment 1.

Here, it is assumed that two cubes, which are imaging target objects, are placed at a distance in the y-axis direction, as shown in FIG. 19A. It is also assumed that the distance between the two cubes is smaller than the spatial resolution in the C-plane that is parallel to the scanning direction of the ultrasonic probe 101, and greater than the spatial resolution in the B-plane that is perpendicular to the scanning direction of the ultrasonic probe 101.

A plurality of ultrasonic images 201 are generated by scanning the target objects in two directions that are y-axis direction and x-axis direction. FIG. 9A and FIG. 9B each shows the ultrasonic images 201 generated by scanning in the y-axis direction and the x-axis direction. In FIG. 9B, the specific cross-section 351 is identified. The specific cross-section 351 is not identical to any one of the ultrasonic images 201.

In this case, the reference image selecting unit 196 selects the reference image 361 located immediately preceding the specific cross-section 351 and the reference image 362 located immediately succeeding the specific cross-section 351, based on the distance and the orientation difference from the specific cross-section 351.

FIG. 9C shows two reference images 361 and 362, and the cross-sectional image 205 of the specific cross-section generated from the two reference images 361 and 362. As shown in FIG. 9C, two target objects are separated in the cross-sectional image 205. The reference images 361 and 362 correspond to the B-plane. By combining pixel values of the reference images 361 and 362 which have resolution of the B-plane, the cross-sectional image 205 having resolution close to that of the B-plane can be obtained.

On the other hand, as described earlier, two target objects cannot be separated in the cross-sectional image generated by the ultrasonic image generating device according to a reference example.

As described, the ultrasonic image generating device 100 according to Embodiment 1 disclosed herein is capable of generating specific cross-sectional images with high resolution. In other words, the ultrasonic image generating device 100 is capable of increasing the accuracy of the cross-sectional image 205.

It has been described that scanning with the ultrasonic probe 101 is linearly performed in the x-direction and the y-direction in FIG. 9A to FIG. 9C for ease of explanation; however, the same advantageous effects can be obtained also in the case where scanning with the ultrasonic probe 101 is freely performed in any directions by a probe user. In this case, even though the obtainment order of the ultrasonic images 201 are used (even though immediately preceding and immediately succeeding frames are simply used) for synthesizing respective pixels in the specific cross-section 351, the specific cross-section 351 does not have higher resolution. Thus, Embodiment 1 provides more marked effects in such a case.

Figure 10:
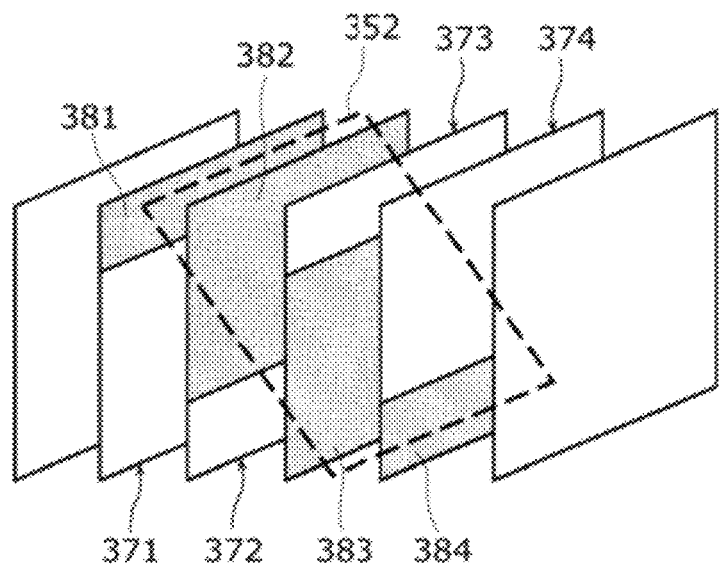
FIG. 10 is a diagram illustrating an example where reference images are selected, according to Embodiment 1.

FIG. 10 is a diagram illustrating another example of the specific cross-section 351. When the specific cross-section 351 shown in FIG. 10 is identified, four reference images 371 to 374 are selected. The pixels of the reference regions 381 to 384 included in the four reference images 371 to 374 are used as reference pixels for the synthesis of the target pixels.

As described above, the ultrasonic image generating device 100 according to Embodiment 1 disclosed herein selects reference images used for the combining, based on the similarity degree of the positional information 203 such as the distance between the specific cross-section 351 and the ultrasonic image 201 and their orientations. As a result, when there are ultrasonic images 201 having the positional information 203 close to that of the specific cross-section 351, it is possible to generate a cross-sectional image 205 having resolution close to that of the B-plane.

Hereinafter, a Variation of Embodiment 1 is described.

First, a description is given of the operations performed when the 3D vibrating probe or the matrix array probe is used as the ultrasonic probe 101.

When the 3D vibrating probe is used, ultrasonic probe elements arranged in line vibrate in the probe. As a result, two-dimensional ultrasonic images can be continuously obtained. With use of the ultrasonic images, it is possible to create images of a three-dimensional region beneath the probe. The obtained two-dimensional ultrasonic images are the same as the images obtained by the linear array probe. By assuming these two-dimensional ultrasonic images as the ultrasonic images 201, the processing same as the processing above can be performed. It is to be noted that the positional information 203 of the ultrasonic image 201 depends on the position and the orientation of the ultrasonic probe elements (ultrasonic transducers) in the probe at the time of the obtainment of the ultrasonic image 201, in addition to the probe positional information. Accordingly, the positional information obtaining unit 110 obtains information on the position and the orientation of the ultrasonic probe elements, in addition to the probe positional information (the position and the orientation of the ultrasonic probe). The positional information obtaining unit 110 calculates the positional information 203 of the ultrasonic image 201 by adding, as offset values, the position and the orientation of the ultrasonic probe elements to the position and the orientation of the ultrasonic probe 101.

When the matrix array probe is used, the ultrasonic probe elements do not physically move in the probe, but the matrix array probe is the same as the 3D vibrating probe in that images of the 3D region beneath the probe are created. Thus, the matrix array probe can be treated in the same way as the 3D vibrating probe by dividing the created 3D region image into a plurality of frames, and taking into account the positional information of each frame.

Figure 11:
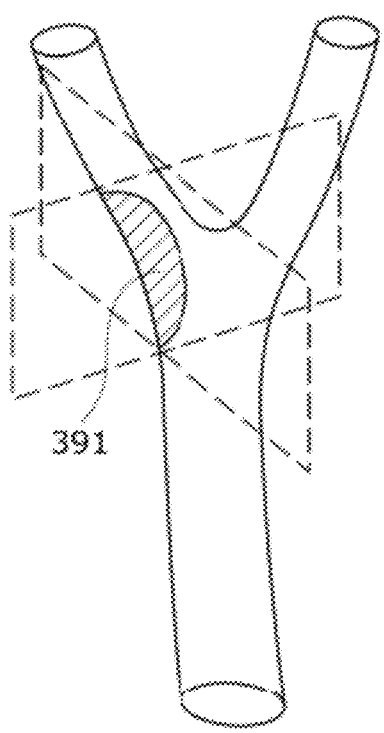
FIG. 11 is a diagram illustrating another example of a volume image obtained by the ultrasonic image generating device according to Embodiment 1.

In the above description, the diagnostic target is the breast; however, the diagnostic target may be parts or organs other than the breast, such as liver, carotid artery, or prostate gland. FIG. 11 is a diagram illustrating an example of a volume image in the case where the diagnostic target is the carotid. In this case, the ROI is a plaque 391 formed in the carotid and the neighboring regions Here, the plaque refers to a protruded lesion where tunica intima and tunica media of a blood vessel are thickened. The plaques have various forms, such as thrombus, fatty plaque, or fibrous plaque, and may cause carotid stenosis, carotid occlusion, cerebral infarction, or cerebral ischemia. As arteriosclerosis develops, plaque is readily formed. Arteriosclerosis is considered to systemically develop; and thus, superficial carotid artery is mainly measured for determining the presence or absence of plaque.

In the above description, optical units such as the camera and the optical marker are used as a unit for obtaining the positional information 203; however, any other units may be used such as a magnetic sensor, an acceleration sensor, a gyro sensor, or a robotic arm. Different types of units for obtaining positional information may be used in combination in a case where a single unit provides insufficient performance. One example is a case where the optical marker is hidden behind a user's hand or the like, causing the optical marker to be in the blind angle of the camera and resulting in not allowing the optical unit to provide positional information. The positional information is not limited to six parameters of the position and the orientation. For example, in the case where the movement direction is limited to a certain axis, only necessary parameters may be obtained and used.

The above description describes the method where the ultrasonic image generating device 100 displays the volume image 206, and the user identifies a specific cross-section from the volume image 206; however, the specific cross-section may be identified by any other methods. For example, it may be that scanning with the ultrasonic probe 101 is performed by a method such as a freehand scanning, and then the ultrasonic image generating device 100 displays respective B-plane images. A user identifies the B-plane image which shows the ROI from the displayed B-plane images. Then, the ultrasonic image generating device 100 may identify a specific cross-section such that an image of a neighboring region (for example, region having an angle of 0 degree or more and less than 360 degrees) of the identified B-plane image.

It may also be that the ultrasonic image generating device 100 adopts the image generating method according to Embodiment 1 when the specific cross-section includes the ROI, and select reference images simply based only on the information of distance from the ROI when the specific cross-section does not include the ROI.

Figure 12:
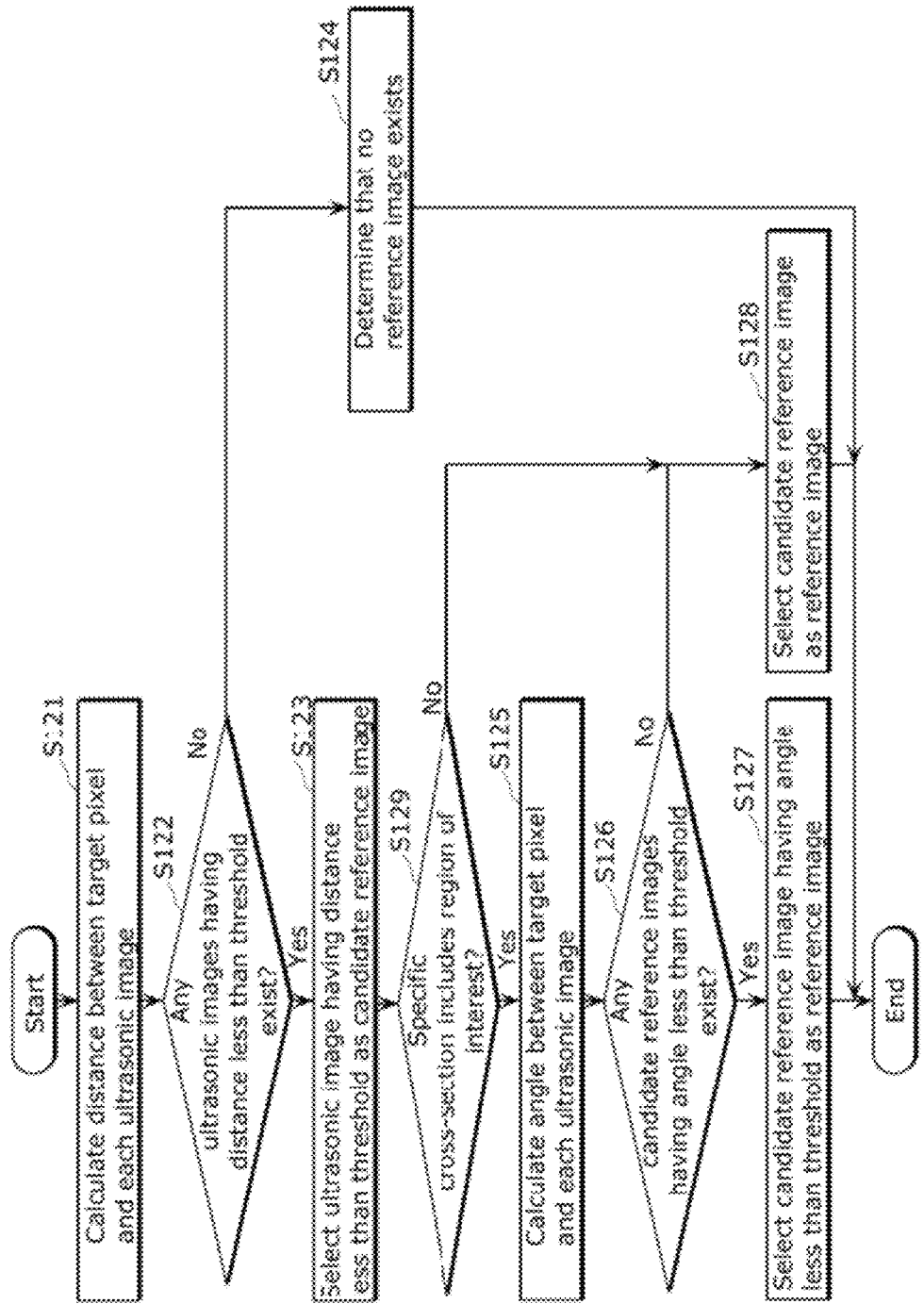
FIG. 12 is a flowchart of a variation of the processing for selecting reference images according to Embodiment 1.

FIG. 12 is a flowchart of the operations of the reference image selecting unit 196 in this case. The processing shown in FIG. 12 includes Step S129 in addition to the processing shown in FIG. 6. More specifically, the reference image selecting unit 196 determines whether or not the specific cross-section includes the ROI after selecting the candidate reference images in Step S123 (S129).

When the specific cross-section includes the ROI (Yes in S129), the reference image selecting unit 196 selects the reference images according to the angle between each candidate reference image and the specific cross-section, in the same manner as in FIG. 6 (S125 to S128). When the specific cross-section includes the ROI (Yes in S129), the reference image selecting unit 196 selects the candidate reference images as reference images (S128).

In other words, when the specific cross-section identified in the volume image 206 includes the ROI, the reference image selecting unit 196 selects the reference images using the information of the distance from the specific cross-section, and the information of the orientation difference from the specific cross-section. When the specific cross-section does not include the ROI, the reference image selecting unit 196 selects the reference images using only the distance information, without using the information of orientation difference from the specific cross-section.

For displaying the volume image 206 such that the inside of the volume image 206 is transparently viewed, cutting out only the neighboring region of the ROT increases visibility of the ROT. Thus, the ultrasonic image generating device 100 may generate the volume image 206 by cutting out only the neighboring region of the ROI for display.

In Embodiment 1, one or more ultrasonic images are extracted which have the distance and the angle difference from a target pixel that are equal to or less than a threshold, and each of the extracted ultrasonic images is weighed before being used; however, all of the extracted pixels do not need to be used. For example, in the case where scores are set to each of the extracted ultrasonic images, only some of the ultrasonic images which have higher matching degree may be used.

In addition, it may be that the ultrasonic image generating device 100 determines images which have similar position and orientation from among the ultrasonic images 201 stored in the image memory 108 or 195, and one of the similar images may be deleted. As a result, the amount of the image memory 108 or 195 may be reduced.

Furthermore, it may be that the ultrasonic image generating device 100 stores only the ultrasonic images 201 which include the ROI in the image memory 195. As a result, the amount of the image memory 195 can be reduced.

Furthermore, the division between the ultrasonic image generating device 100 (main unit) and the ultrasonic probe 101 shown in FIG. 3 is merely an example, and the present disclosure is not limited to this example. For example, it may be defined that a system which includes the ultrasonic probe 101 and the main unit (the ultrasonic image generating device 100 shown in FIG. 3) is an ultrasonic image generating device. It may also be that the ultrasonic probe 101 includes part of the processing units included in the main unit.

The example has been described where B-mode images are mainly used as the ultrasonic images 201; however, it may be that Doppler images (Doppler data) which indicate blood flow or the like may be used instead of the B-mode images.

Figure 13:
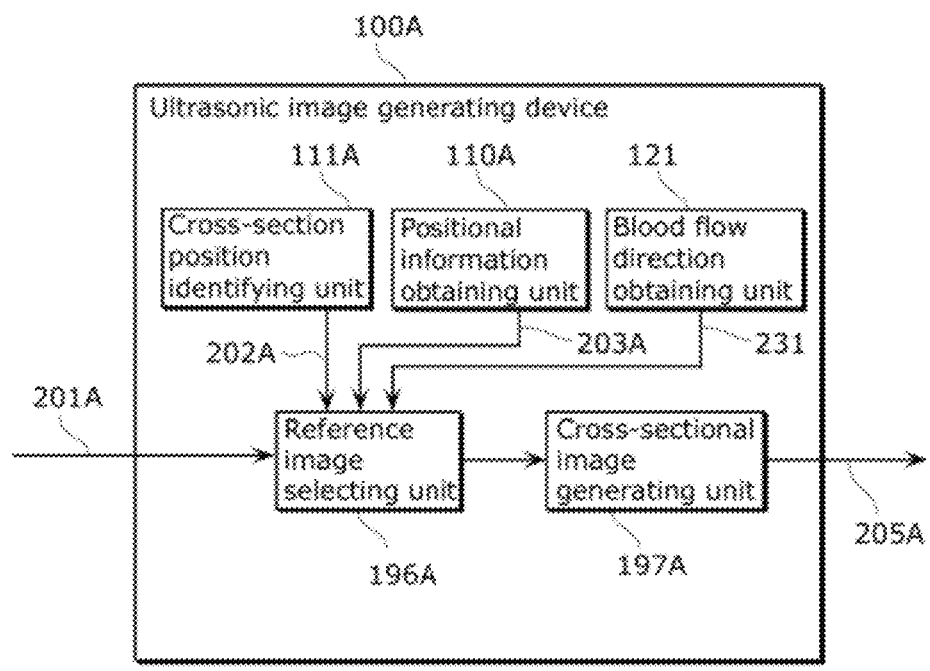
FIG. 13 is a block diagram of a variation of the ultrasonic image generating device according to Embodiment 1.

FIG. 13 is a block diagram schematically illustrating a configuration of an ultrasonic image generating device 100A in this case.

The ultrasonic image generating device 100A generates a cross-sectional image 205A indicating blood flow in the specific cross-section of a subject from a plurality of Doppler images 201A which are obtained from the scanning of the subject from different directions using the ultrasonic probe 101, and which indicate the blood flow (indicate the flow velocity and direction). The ultrasonic image generating device 100A includes a cross-sectional position identifying unit 111A, a blood flow direction obtaining unit 121, a positional information obtaining unit 110A, a reference image selecting unit 196A, and a cross-sectional image generating unit 197A.

The cross-sectional position identifying unit 111A obtains cross-section information 202A indicating the position of the specific cross-section.

The blood flow direction obtaining unit 121 obtains blood flow information 231 which indicates the direction of the blood flow in the specific cross-section. The information of the blood flow direction can be obtained by using, for example, a method specified by a user, or a method where Doppler images or B-mode images are analyzed to automatically detect the blood vessel running position and direction.

The positional information obtaining unit 110A obtains positional information 203A including respective positions and orientations of the Doppler images 201A of the subject.

The reference image selecting unit 196A selects at least one of the Doppler images 201A as a reference image. The selected Doppler images 201A each has a distance from the specific cross-section that is less than a first threshold, and has an orientation different from the direction of the blood flow by less than a second threshold.

The cross-sectional image generating unit 197 generates the cross-sectional image 205A using the reference images.

Figure 14:
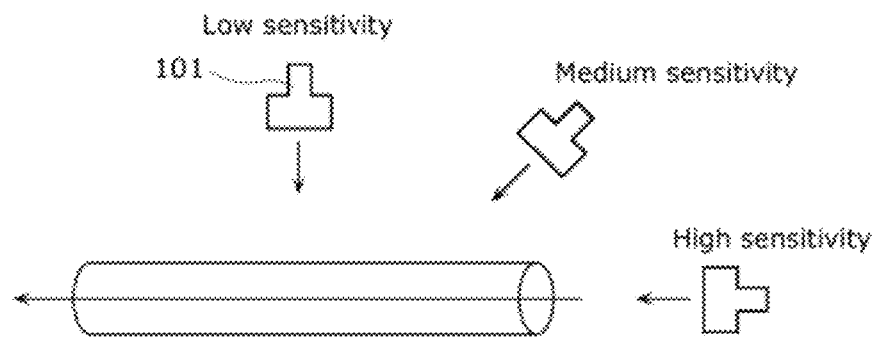
FIG. 14 is a diagram illustrating sensitivity of a Doppler image according to Embodiment 1.

As shown in FIG. 14, measurement sensitivity varies depending on the difference between the orientation of the ultrasonic probe 101 and the direction of the blood flow. More specifically, as the difference between the direction of the blood flow and the direction of the ultrasonic waves emitted from the ultrasonic probe 101 decreases, the sensitivity increases. As a result, the accuracy of the cross-sectional image 205A can be increased by generating the cross-sectional image 205A using the Doppler images 201A each having a an orientation different from the direction of the blood flow by less than the second threshold.

Detailed configuration of the ultrasonic image generating device 100A are the same as the ultrasonic image generating device 100 with the "orientation of the specific image" being replaced with the "direction of the blood"; and thus, their detailed description are not repeated.

The ultrasonic image generating device and method according to the present disclosure have been described based on Embodiment 1; however, the present disclosure is not limited to the embodiment. The present disclosure includes variations came up by those in the art applied in the present embodiments in a range of the arguments disclosed herein.

Embodiment 2

The processing described in Embodiment 1 can be easily performed in an independent computer system by recording a program for implementing the image generating method described in Embodiment 1 on a recording medium such as a flexible disk.

Figure 15A:
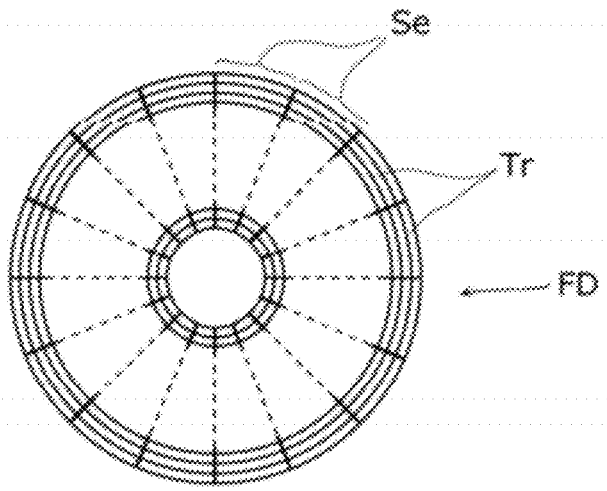
FIG. 15A is a diagram illustrating a flexible disk according to Embodiment 2.
Figure 15B:
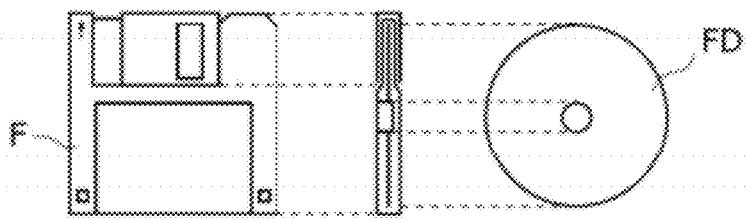
FIG. 15B is a diagram illustrating a structure of the flexible disk according to Embodiment 2.
Figure 15C:
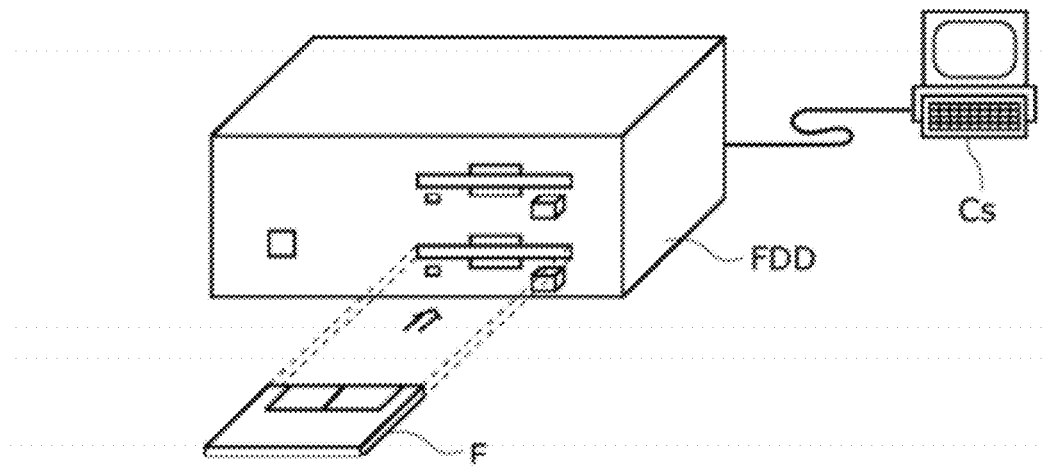
FIG. 15C is a diagram illustrating a computer system according to Embodiment 2.

FIG. 15A to FIG. 15C each is a diagram illustrating a case where the image generating method according to Embodiment 1 is implemented in a computer system, using the program recorded on the recording medium such as a flexible disk.

FIG. 15A illustrates an example of a physical format of the flexible disk that is a recording medium body. FIG. 15B illustrates an external front view and a cross-sectional view of a flexible disk and the flexible disk. A flexible disk RD is contained in a case F. A plurality of tracks Tr are formed concentrically on the surface of the disk from the periphery into the inner radius of the disk. Each track Tr is divided into 16 sectors Se in the angular direction. Accordingly, in the flexible disk FD which stores the program, the program is recorded on sectors assigned to the flexible disk FD.

FIG. 15C illustrates a structure for recording and reproducing the program on the flexible disk FD. When the program for implementing the image generating method is recorded on the flexible disk FD, the computer system Cs writes the program on the flexible disk FD via a flexible disk drive FDD. When the image generating method is constructed in the computer system Cs using the program on the flexible disk FD, the program is read out from the flexible disk FD using the flexible disk drive FDD and is transferred to the computer system Cs.

The above description is given on an assumption that a recording medium is a flexible disk, but an optical disk may be used instead. In addition, the recording medium is not limited to the flexible disk and the optical disk. As long as the program is recorded, any recording medium may be used, such as an IC card and a ROM cassette.

The block such as the image processing unit 109 in FIG. 3 is typically implemented as a Large Scale Integration (LSI) that is an integrated circuit. The LSIs may be separately made into one chip, or each LSI may be partly or entirely made into one chip.

The LSI may also be referred to IC, system LSI, super LSI, or ultra LSI depending on the degree of integration.

Moreover, ways to achieve integration are not limited to the LSI. A dedicated circuit or a general-purpose processor may also achieve the integration. For example, a dedicated circuit for graphics such as a graphic processing unit (GPU) may be used. Field Programmable Gate Array (FPGA) that can be programmed after manufacturing an LSI or a reconfigurable processor that allows re-configuration of the connection or configuration of a circuit cell in an LSI can be used for the same purpose.

Furthermore, in the future, with advancement in semiconductor technology, a brand-new technology may replace LSI. The functional blocks may be integrated using such a technology. The possibility is that the present disclosure is applied to biotechnology.

Furthermore, at least part of the ultrasonic image generating device according to the above exemplary embodiments and the functions of the variations may be combined.

Furthermore, the numbers cited above are used simply to specifically describe the present disclosure, and the present disclosure is not limited thereto.

The divisions of the functional blocks in the block diagrams are an example. It may be that a plurality of functional blocks are implemented as a single functional block, one functional block is divided into blocks, or part of the functions is moved to other functional blocks. The functions of the functional blocks having similar functions may be processed by a single hardware or software in parallel or in a time-sharing manner.

The described executing order of the steps is merely an example for specifically describing the present disclosure, and the order is not limited thereto. Part of the steps may be executed simultaneously (in parallel) with other steps.

Those skilled in the art will readily appreciate that many variations are possible in the exemplary embodiments without materially departing from the novel teachings and advantages of the present disclosure. Accordingly, all such variations are intended to be included within the scope of the present disclosure.

The herein disclosed subject matter is to be considered descriptive and illustrative only, and the appended Claims are of a scope intended to cover and encompass not only the particular embodiment(s) disclosed, but also equivalent structures, methods, and/or uses.

INDUSTRIAL APPLICABILITY

An ultrasonic image generating device and an image generating method according to one or more exemplary embodiments disclosed herein has high availability particularly in medical diagnostic device industries.

The invention claimed is:

1. An ultrasonic image generating device comprising:
an ultrasonic probe which acquires a plurality of ultrasonic images obtained by scanning a subject from a plurality of directions with the ultrasonic probe; and
a processing circuit which is configured to:
obtain cross-section information indicating a position and an orientation of a specific cross-section of the subject;
obtain positional information including a position and an orientation of each of the ultrasonic images of the subject;
select at least one of the ultrasonic images originally obtained by the ultrasonic probe as a reference image, wherein the at least one of the ultrasonic images is separated from the specific cross-section by a distance that is less than a first threshold and has an orientation that is different from the orientation of the specific cross-section by less than a second threshold; and
generate a cross-sectional image of the specific cross-section by calculating a pixel value of the cross-sectional image from an original pixel value of the reference image.

2. The ultrasonic image generating device according to claim 1, wherein the specific cross-section includes a region of interest, and the processing circuit is configured to select, as the reference image, an ultrasonic image from among the ultrasonic images obtained by the ultrasonic probe that is separated from a point included in the region of interest in the specific cross-section by a distance that is less than the first threshold and has an orientation that is different from the orientation of the specific cross-section by less than the second threshold.

3. The ultrasonic image generating device according to claim 1, wherein the processing circuit is configured to select an ultrasonic image as the reference image from the ultrasonic images, for each of a plurality of regions of the specific cross-section which are obtained by dividing the specific cross-section, the ultrasonic images selected as the respective reference images each being separated from the corresponding region by a distance that is less than the first threshold and each having an orientation that is different from the orientation of the specific cross-section by less than the second threshold, and
wherein the processing circuit is configured to generate an image of each of the regions using the corresponding reference image selected for the region.

4. The ultrasonic image generating device according to claim 3, wherein the ultrasonic images selected as the respective reference images are each separated from a central point of the corresponding region by a distance that is less than the first threshold and each have an orientation that is different from the orientation of the specific cross-section by less than the second threshold.

5. The ultrasonic image generating device according to claim 1, wherein the processing circuit is configured to obtain a position and an orientation of the ultrasonic probe, and to calculate the positional information based on the position and the orientation of the ultrasonic probe.

6. The ultrasonic image generating device according to claim 5, wherein the processing circuit is further configured to obtain a direction of ultrasonic waves emitted from the ultrasonic probe, and to calculate the positional information based on the direction of the ultrasonic waves and the position and the orientation of the ultrasonic probe.

7. The ultrasonic image generating device according to claim 1, wherein the first threshold is less than or equal to a spatial resolution in a C-plane that is parallel to a scanning direction of the ultrasonic probe, and the second threshold is less than or equal to 30 degrees.

8. The ultrasonic image generating device according to claim 1, wherein, when the ultrasonic images do not include the ultrasonic image that is separated from the specific cross-section by a distance that is less than the first threshold and that has an orientation that is different from the orientation of the specific cross-section by less than the second threshold, the processing circuit is configured to generate the cross-sectional image using an ultrasonic image which is included in the ultrasonic images and is separated from the specific cross-section by a smallest distance among the ultrasonic images.

9. The ultrasonic image generating device according to claim 1, wherein the processing circuit is further configured to generate a volume image from the ultrasonic images, and to generate the cross-section information indicating the specific cross-section which is identified by a user with respect to the volume image.

10. The ultrasonic image generating device according to claim 1, wherein the reference image includes a plurality of reference images, and the processing circuit is configured to (i) generate a pixel value of a pixel included in the cross-sectional image by multiplying a pixel value of a pixel included in each of the reference images by a weighting coefficient and summing resulting pixel values, and (ii) increase the weighting coefficient for a reference image having a smaller orientation difference from the specific cross-section among the reference images.

11. The ultrasonic image generating device according to claim 10, wherein the processing circuit is configured to increase the weighting coefficient for a reference image having a smaller orientation difference from the specific cross-section, the reference image being included in the reference images and being separated from the specific cross-section by a distance that is less than a third threshold.

12. An ultrasonic image generating device, comprising:

an ultrasonic probe which acquires a plurality of ultrasonic images obtained by scanning a subject from a plurality of directions with the ultrasonic probe; and a processing circuit which is configured to:

obtain cross-section information indicating a position and an orientation of a specific cross-section of the subject;

obtain positional information including a position and an orientation of each of the ultrasonic images of the subject;

select at least one of the ultrasonic images originally obtained by the ultrasonic probe as a reference image, wherein the processor or circuit is configured to (i) select, as the reference image, an ultrasonic image that is separated from the specific cross-section by a distance that is less than a first threshold and has an orientation that is different from the orientation of the specific cross-section that is less than a second threshold, when a region of interest is specified in the specific cross-section, and (ii) select the reference image based only on the distance of separation from the specific cross-section, when a region of interest is not specified in the specific cross-section; and generate a cross-sectional image of the specific cross-section by calculating a pixel value of the cross-sectional image from an original pixel value of the reference image.

13. An image generation method for an ultrasonic image generating device which comprises an ultrasonic probe and a processing circuit, the method comprising:

acquiring, using the ultrasonic probe, a plurality of ultrasonic images obtained by scanning a subject from a plurality of directions with the ultrasonic probe;

obtaining, using the processing circuit, cross-section information indicating a position and an orientation of a specific cross-section of the subject;

obtaining, using the processing circuit, positional information including a position and an orientation of each of the ultrasonic images of the subject;

selecting, using the processing circuit, at least one of the ultrasonic images originally obtained by the ultrasonic probe as a reference image, the at least one of the ultrasonic images being separated from the specific cross-section by a distance that is less than a first threshold and having an orientation that is different from the orientation of the specific cross-section by less than a second threshold; and generating, using the processing circuit, a cross-sectional image of the specific cross-section by calculating a pixel value of the cross-sectional image from an original pixel value of the reference image.

* * * * *